US011674178B2

(12) United States Patent
Mohammed et al.

(10) Patent No.: US 11,674,178 B2
(45) Date of Patent: Jun. 13, 2023

(54) METHODS AND COMPOSITIONS FOR SEQUENTIALLY DETECTING TARGETS

(71) Applicant: Ultivue, Inc., Cambridge, MA (US)

(72) Inventors: Abdul Majeed Mohammed, Cambridge, MA (US); Mael Manesse, Medford, MA (US); Mack J. Schermer, Arlington, MA (US); Mark N. Bobrow, Lexington, MA (US); Michael Jules Natan, Weston, MA (US)

(73) Assignee: Ultivue, Inc., Cambridge, MA (US)

( * ) Notice: Subject to any disclaimer, the term of this patent is extended or adjusted under 35 U.S.C. 154(b) by 497 days.

(21) Appl. No.: 16/713,760

(22) Filed: Dec. 13, 2019

(65) Prior Publication Data

US 2020/0190583 A1 Jun. 18, 2020

Related U.S. Application Data

(60) Provisional application No. 62/780,038, filed on Dec. 14, 2018.

(51) Int. Cl.
*C12Q 1/6876* (2018.01)
*G01N 21/76* (2006.01)

(52) U.S. Cl.
CPC ........... *C12Q 1/6876* (2013.01); *G01N 21/76* (2013.01)

(58) Field of Classification Search
None
See application file for complete search history.

(56) References Cited

U.S. PATENT DOCUMENTS

| | | | |
|---|---|---|---|
| 5,403,711 A | 4/1995 | Walder et al. | |
| 6,316,229 B1 | 11/2001 | Lizardi et al. | |
| 6,750,964 B2 | 6/2004 | Levenson et al. | |
| 9,944,972 B2 | 4/2018 | Yin et al. | |
| 10,190,151 B2 | 1/2019 | Yin et al. | |
| 2004/0009612 A1 | 1/2004 | Zhao et al. | |
| 2004/0253593 A1* | 12/2004 | Cai | C12Q 1/6823 435/6.11 |
| 2006/0024695 A1 | 2/2006 | Li et al. | |
| 2010/0330573 A1* | 12/2010 | Larson | C12Q 1/689 435/6.15 |
| 2011/0223592 A1* | 9/2011 | Collis | C12Q 1/6816 435/6.12 |
| 2012/0122714 A1* | 5/2012 | Samuels | G01N 33/532 506/18 |
| 2014/0178875 A1* | 6/2014 | Fuchs | C12Q 1/6841 435/287.2 |
| 2015/0004598 A1* | 1/2015 | Gao | C12Q 1/6804 435/6.11 |
| 2015/0267251 A1 | 9/2015 | Cai et al. | |
| 2018/0164308 A1 | 6/2018 | Walter et al. | |
| 2018/0372736 A1 | 12/2018 | Hennek et al. | |

FOREIGN PATENT DOCUMENTS

| | | |
|---|---|---|
| EP | 1586662 A1 | 10/2005 |
| WO | 2015138653 A1 | 9/2015 |
| WO | 2017143006 A1 | 8/2017 |
| WO | 2018107054 A1 | 6/2018 |

OTHER PUBLICATIONS

Agasti et al., "DNA-barcoded labeling probes for highly multi-plexed Exchange-PAINT imaging," Chem Sci, 8(4):3080-3091 (2017).
Choi et al., "Next-Generation in Situ Hybridization Chain Reaction: Higher Gain, Lower Cost, Greater Durability," American Chemical Society 8(5):4284-4294 (2014).
Dirks et al., "Triggered amplification by hybridization chain reaction," PNAS 101(43):15275-15278 (2004).
Gusev et al., "Rolling Circle Amplification: A New Approach to Increase Sensitivity for Immunohistochemistry and Flow Cytometry," Am. J. Pathology 159(1):63-9 (2001).
Hofacker, "Vienna RNA secondary structure server," Nucleic Acids Research 31(13):3429-3431 (2003).
International Search Report and Written Opinion issued in PCT/US2019/066259, dated Aug. 31, 2020, 10 pages.
Jungmann et al., "Multiplexed 3D Cellular Super-Resolution Imaging with DNA-PAINT and Exchange-PAINT," Nat Methods. 11(3):313-318 (2014).
Kishi et al., "Programmable autonomous synthesis of single-stranded DNA," Nat Chem 10(2):155-164 (2018).
Li, et al., "Quenched Stochastic Optical Reconstruction Microscopy (qSTORM) with Graphene Oxide," Sci Rep 8, 16928(2018).
Lutz et al., "Versatile multiplexed super-resolution imaging of nanostructures by Quencher-Exchange-PAINT," Nano Res. 11, 6141-6154 (2018).
Olejnik et al., "Photocleavable peptide-DNA conjugates: synthesis and applications to DNA analysis using MALDI-MS," Nucleic Acids Res. 27(23):4626-31 (1999).

(Continued)

*Primary Examiner* — Amanda Haney
(74) *Attorney, Agent, or Firm* — McNeill Baur PLLC

(57) ABSTRACT

Compositions, kits and methods for detecting a plurality of targets are provided herein. A probe-set composition is provided, including one or more first probes and one or more second probes. Each of the first probe includes a nucleic acid sequence complementary to a nucleic acid barcode of a corresponding target-specific binding partner, a first label, and a cleavage site for a first cleavage agent, wherein the first cleavage agent is capable of releasing the first label. Each of the second probes includes a nucleic acid sequence complementary to a nucleic acid barcode of a corresponding target-specific binding partner, a second label, a quench moiety that renders the second label undetectable, and a cleavage site for the first cleavage agent. The first cleavage agent is capable of releasing the quench moiety, whereby the second label is rendered detectable.

16 Claims, 19 Drawing Sheets

Specification includes a Sequence Listing.

(56) References Cited

OTHER PUBLICATIONS

Schweitzer et al., "Immunoassays with rolling circle DNA amplification: A versatile platform for ultrasensitive antigen detection," PNAS, Aug. 29, 2000, vol. 97, No. 18, pp. 10113-10119.
Schweller et al., "Multiplexed in situ Immunofluorescence via Dynamic DNA Complexes," Angew Chem Int Ed Engl. 51(37): 9292-9296 (2012).
Wang et al., "Rapid sequential in situ multiplexing with DNA-ExchangeImaging in Neuronal Cells and Tissues," Nano Lett. 17(10):6131-6139 (2017).
Yin et al., "Programming biomolecular self-assembly pathways," Nature 451(7176):318-22 (2008), Abstract.
Yu, Y. et al., "Chemoselective peptide modification via photocatalytic tryptophan β-position conjugation," J. Am. Chem. Soc. 140, 6797-6800 (2018), Abstract.

\* cited by examiner

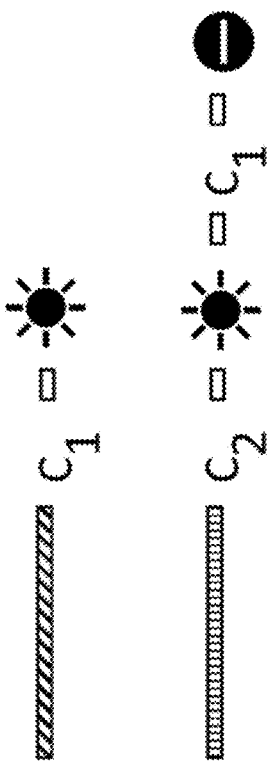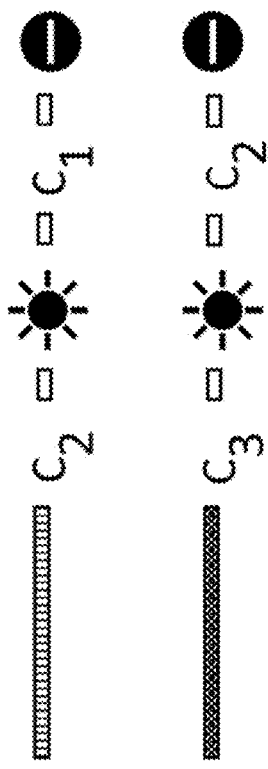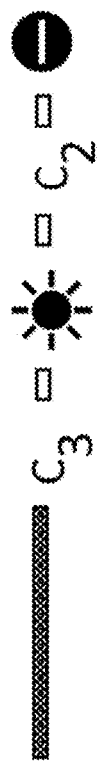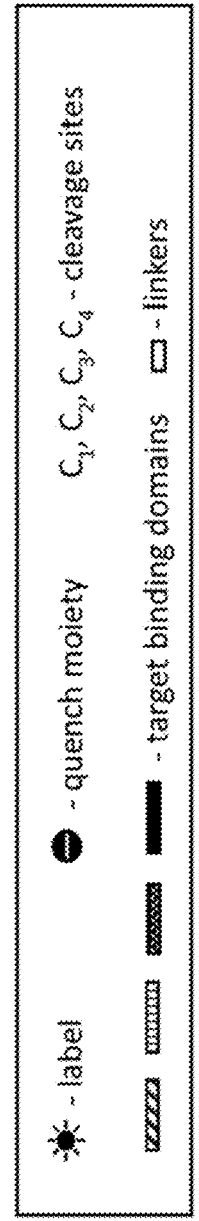
Figure 1A
Figure 1B
Figure 1C
Figure 1D

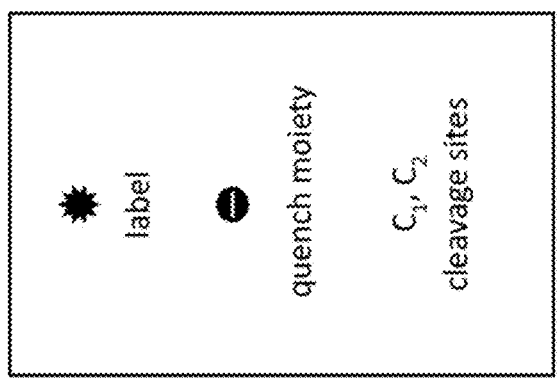
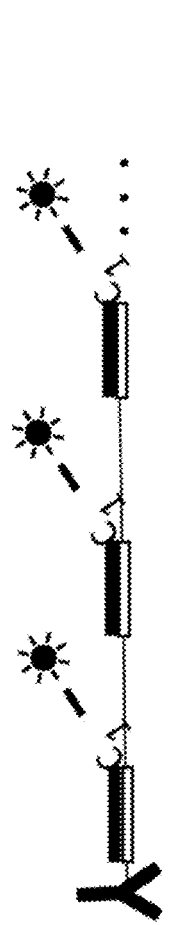
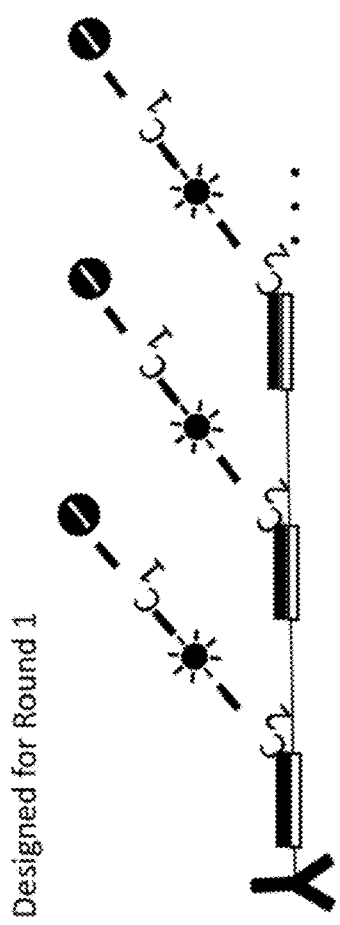
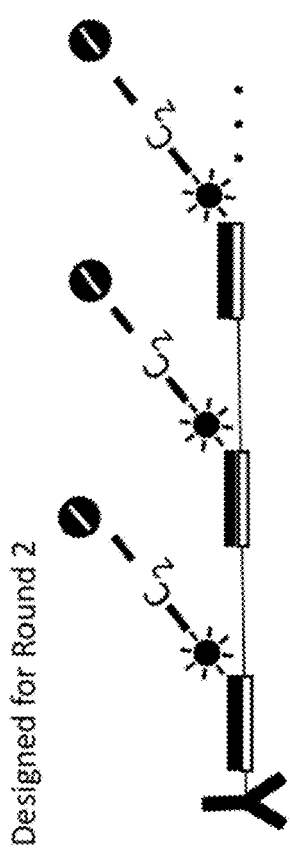
Figure 3A
Figure 3B
Figure 3C

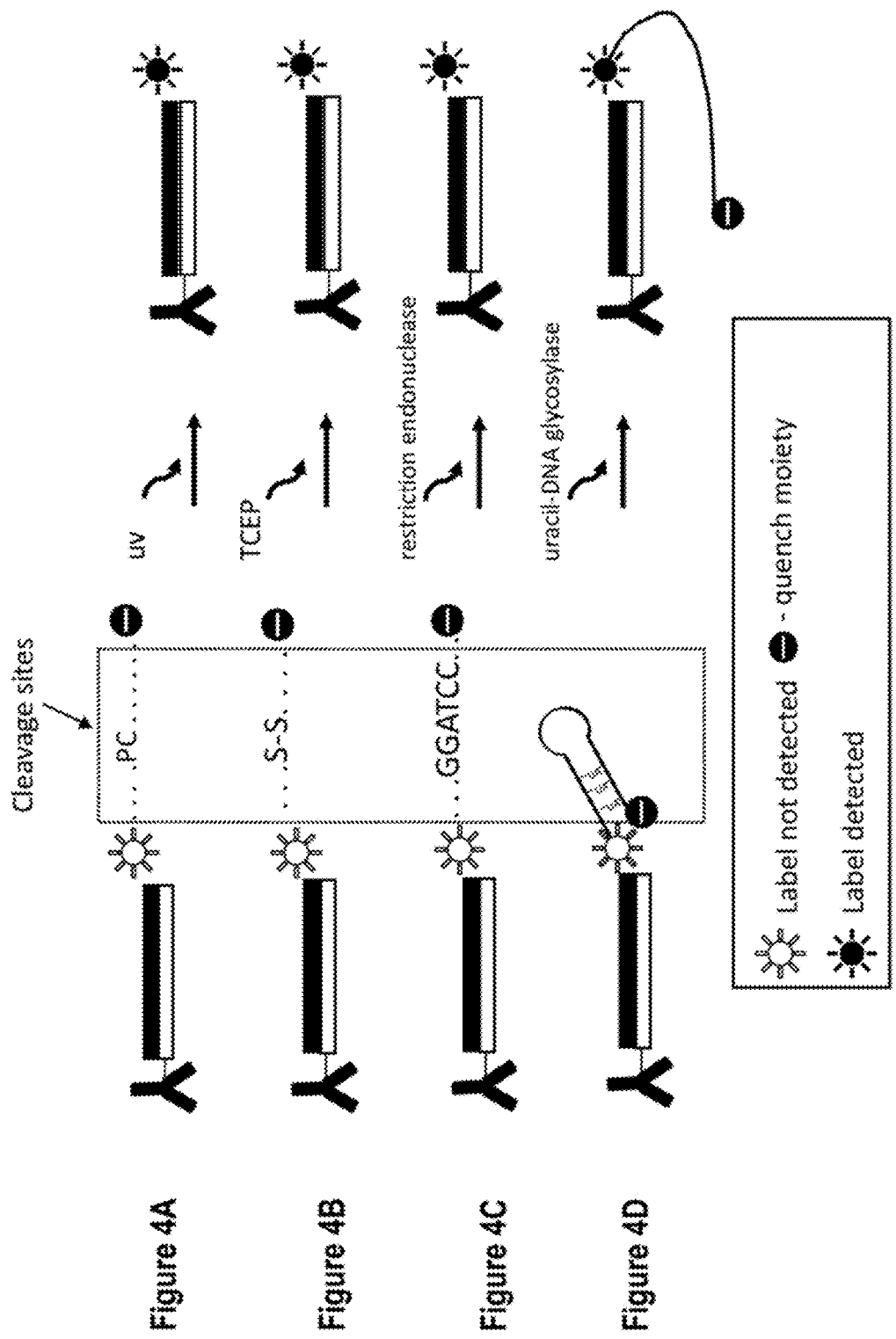

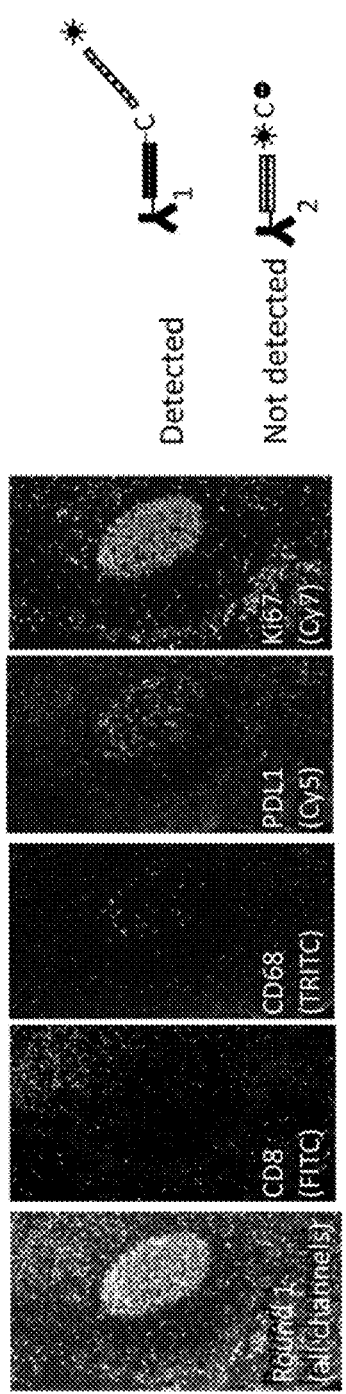
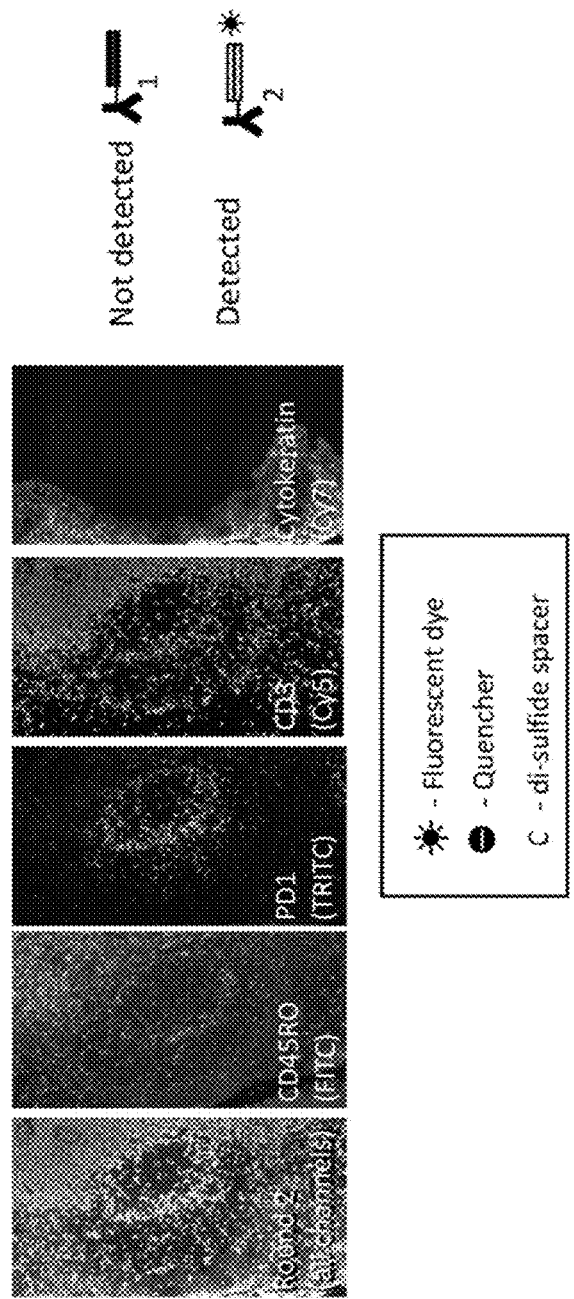
Figure 6A
Figure 6B

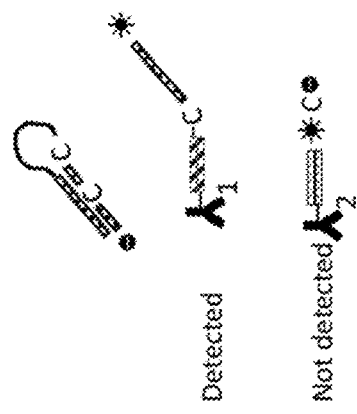
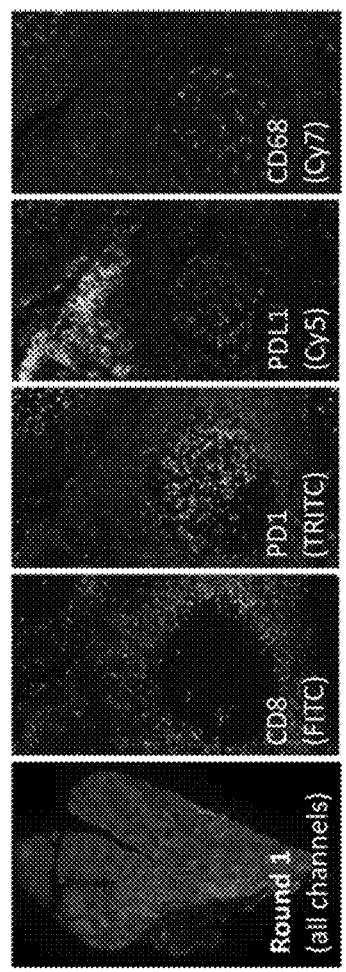
Figure 11B
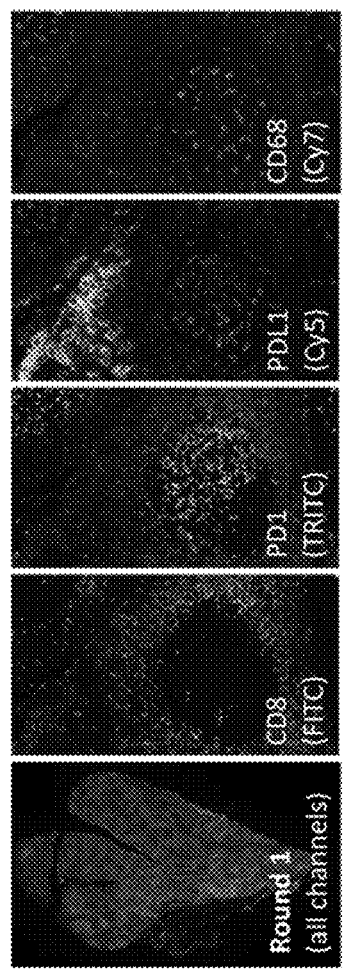
Figure 11C

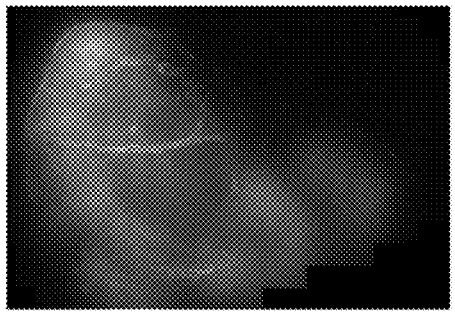
Figure 12B
Figure 12D
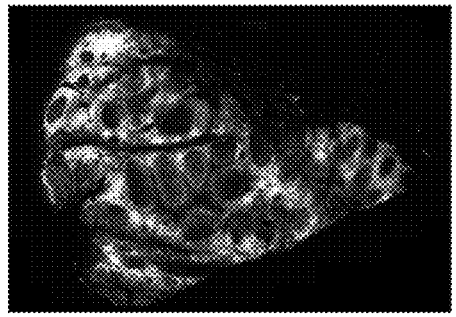
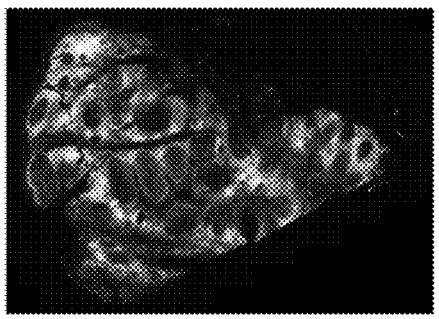
Figure 12A
Figure 12C
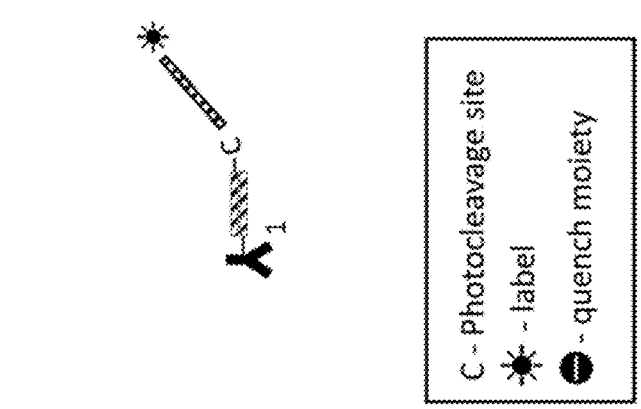
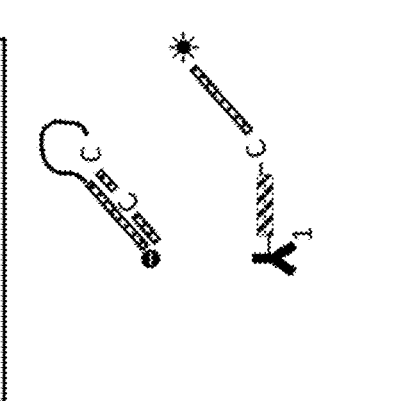

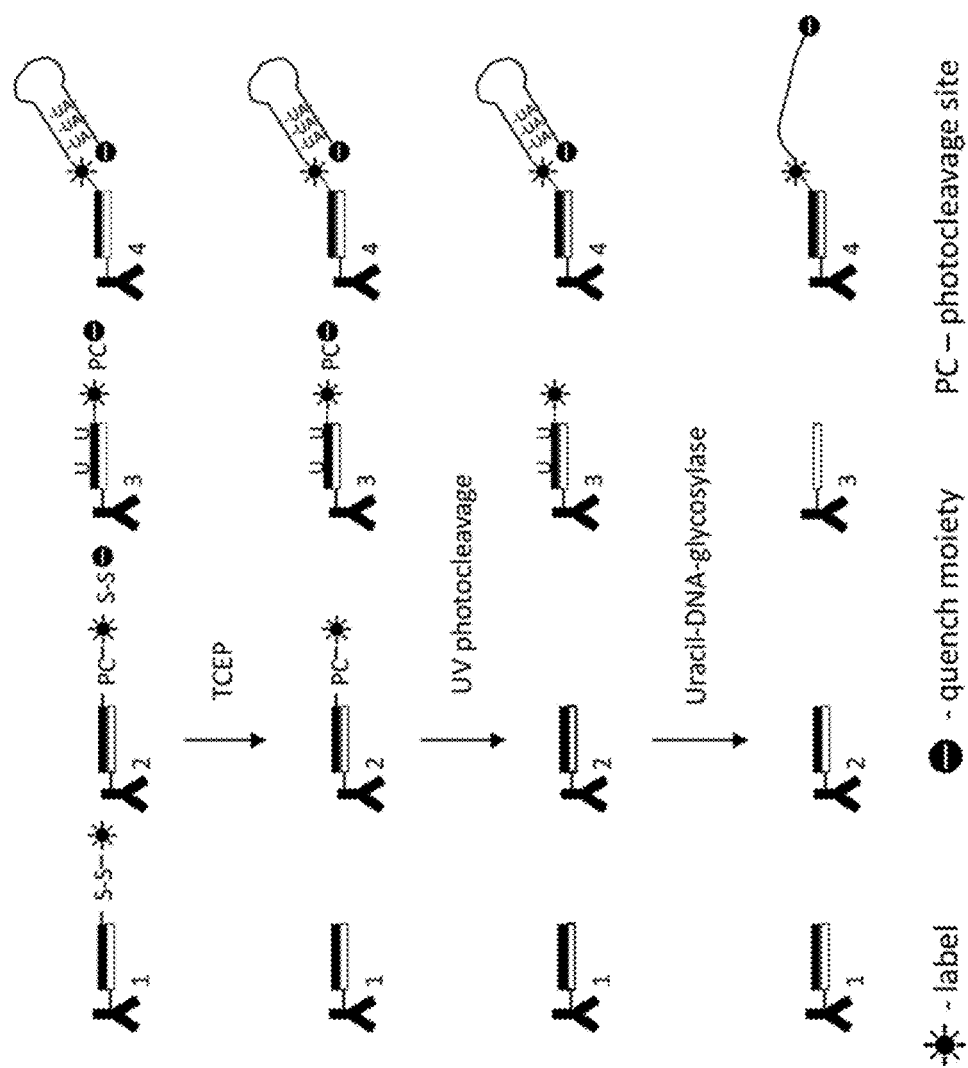

SEQUENCE LISTING

```
<160> NUMBER OF SEQ ID NOS: 27

<210> SEQ ID NO 1
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 1
acggaaccaa ca                                                     12

<210> SEQ ID NO 2
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 2
```
acggaatgag gc                                                           12

<210> SEQ ID NO 3
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 3
acttgctgac ga                                                           12

<210> SEQ ID NO 4
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 4
tcacgtcagc at                                                           12

<210> SEQ ID NO 5
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 5
ttgacgatgg ca                                                           12

<210> SEQ ID NO 6
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 6
gggaagtagg gc                                                           12

<210> SEQ ID NO 7
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 7
cccaaaacgt cg                                                           12

<210> SEQ ID NO 8
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 8
tcgctgtcat ga                                                           12

<210> SEQ ID NO 9
<211> LENGTH: 12
<212> TYPE: DNA

```
<213> ORGANISM: Artificial sequence
<220> FEATURE:
<223> OTHER INFORMATION: Exemplary nucleic acid barcode sequence

<400> SEQUENCE: 9
agcaattcgg gt                                                          12

<210> SEQ ID NO 10
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 10
cgggttaagg gt                                                          12

<210> SEQ ID NO 11
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 11
gcgttgggat ga                                                          12

<210> SEQ ID NO 12
<211> LENGTH: 12
<212> TYPE: DNA
<213> ORGANISM: Artificial sequence
<220> FEATURE:
<223> OTHER INFORMATION: Exemplary nucleic acid barcode sequence

<400> SEQUENCE: 12
agcgaggaaa gt                                                          12

<210> SEQ ID NO 13
<211> LENGTH: 12
<212> TYPE: DNA
<213> ORGANISM: Artificial sequence
<220> FEATURE:
<223> OTHER INFORMATION: Complementary sequence to SEQ ID NO: 1

<400> SEQUENCE: 13
tgttggttcc gt                                                          12

<210> SEQ ID NO 14
<211> LENGTH: 12
<212> TYPE: DNA
<213> ORGANISM: Artificial sequence
<220> FEATURE:
<223> OTHER INFORMATION: Complementary sequence to SEQ ID NO: 2

<400> SEQUENCE: 14
gcctcattcc gt                                                          12

<210> SEQ ID NO 15
<211> LENGTH: 12
<212> TYPE: DNA
<213> ORGANISM: Artificial sequence
<220> FEATURE:
<223> OTHER INFORMATION: Complementary sequence to SEQ ID NO: 3

<400> SEQUENCE: 15
tcgtcagcaa gt                                                          12
```

<210> SEQ ID NO 16
<211> LENGTH: 12
<212> TYPE: DNA
<213> ORGANISM: Artificial sequence
<220> FEATURE:
<223> OTHER INFORMATION: Complementary sequence to SEQ ID NO: 4

<400> SEQUENCE: 16
atgctgacgt ga                                                          12

<210> SEQ ID NO 17
<211> LENGTH: 12
<212> TYPE: DNA
<213> ORGANISM: Artificial sequence
<220> FEATURE:
<223> OTHER INFORMATION: Complementary sequence to SEQ ID NO: 5

<400> SEQUENCE: 17
tgccatcgtc aa                                                          12

<210> SEQ ID NO 18
<211> LENGTH: 12
<212> TYPE: DNA
<213> ORGANISM: Artificial sequence
<220> FEATURE:
<223> OTHER INFORMATION: Complementary sequence to SEQ ID NO: 6

<400> SEQUENCE: 18
gccctacttc cc                                                          12

<210> SEQ ID NO 19
<211> LENGTH: 12
<212> TYPE: DNA
<213> ORGANISM: Artificial sequence
<220> FEATURE:
<223> OTHER INFORMATION: Complementary sequence to SEQ ID NO: 7

<400> SEQUENCE: 19
cgacgttttg gg                                                          12

<210> SEQ ID NO 20
<211> LENGTH: 12
<212> TYPE: DNA
<213> ORGANISM: Artificial sequence
<220> FEATURE:
<223> OTHER INFORMATION: Complementary sequence to SEQ ID NO: 8

<400> SEQUENCE: 20
tcatgacagc ga                                                          12

<210> SEQ ID NO 21
<211> LENGTH: 12
<212> TYPE: DNA
<213> ORGANISM: Artificial sequence
<220> FEATURE:
<223> OTHER INFORMATION: Complementary sequence to SEQ ID NO: 9

<400> SEQUENCE: 21
acccgaattg ct                                                          12

<210> SEQ ID NO 22
<211> LENGTH: 12
<212> TYPE: DNA
<213> ORGANISM: Artificial sequence
<220> FEATURE:

-continued

```
<223> OTHER INFORMATION: Complementary sequence to SEQ ID NO: 10

<400> SEQUENCE: 22
acccttaacc cg                                                          12

<210> SEQ ID NO 23
<211> LENGTH: 12
<212> TYPE: DNA
<213> ORGANISM: Artificial sequence
<220> FEATURE:
<223> OTHER INFORMATION: Complementary sequence to SEQ ID NO: 11

<400> SEQUENCE: 23
tcatcccaac gc                                                          12

<210> SEQ ID NO 24
<211> LENGTH: 12
<212> TYPE: DNA
<213> ORGANISM: Artificial sequence
<220> FEATURE:
<223> OTHER INFORMATION: Complementary sequence to SEQ ID NO: 12

<400> SEQUENCE: 24
actttcctcg ct                                                          12

<210> SEQ ID NO 25
<211> LENGTH: 22
<212> TYPE: DNA
<213> ORGANISM: Artificial sequence
<220> FEATURE:
<223> OTHER INFORMATION: Sequence selective for miR-146a

<400> SEQUENCE: 25
aacccatgga attcagttct ca                                               22

<210> SEQ ID NO 26
<211> LENGTH: 22
<212> TYPE: DNA
<213> ORGANISM: Artificial sequence
<220> FEATURE:
<223> OTHER INFORMATION: Sequence selective for miR-15a

<400> SEQUENCE: 26
cacaaaccat tatgtgctgc ta                                               22

<210> SEQ ID NO 27
<211> LENGTH: 22
<212> TYPE: DNA
<213> ORGANISM: Artificial sequence
<220> FEATURE:
<223> OTHER INFORMATION: Sequence selective for MiR-155

<400> SEQUENCE: 27
cccctatcac gattagcatt aa                                               22
```

METHODS AND COMPOSITIONS FOR SEQUENTIALLY DETECTING TARGETS

CROSS-REFERENCE TO RELATED APPLICATIONS

This application claims the benefit of priority of U.S. Provisional Application No. 62/780,038, filed Dec. 14, 2018, the content of which is incorporated herein by reference in its entirety for any purpose.

SEQUENCE LISTING

The present application is filed with a Sequence Listing in electronic format. The Sequence Listing is provided as a file entitled "2019-12-11_01168-0019-00US_SEQ_List_ST25.txt" created on Dec. 11, 2019, which is 8,192 bytes in size. The information in the electronic format of the sequence listing is incorporated herein by reference in its entirety.

INTRODUCTION

This application relates generally to the field of detection of analytes (e.g., targets), and in particular, relates to compositions, kits and methods for detecting a plurality of targets.

In recent years, methods for examining biologically relevant molecules (known as biomarkers) in tissue samples have improved. The ability to detect increasing numbers of biomarkers has permitted more sophisticated characterization of tissue architecture that, in turn, allows clinicians to better understand and predict an individual's health condition by examining a tissue sample. Whereas previous methods involved examining one biomarker at a time, multiplex immunohistochemistry (IHC) allows spatial profiling of multiple biomarkers in a single tissue sample. IHC involves binding antibodies to biomarkers, attaching fluorescent labels to the antibodies (with each biomarker identified by a different color fluorescent label) and using a fluorescence microscope to image the sample.

DNA Exchange Imaging is an established process for multiplexed detection of biomarkers in tissue samples, which employs multiple rounds of treatment of the tissue. First, DNA-barcoded antibodies are applied to the sample and allowed to bind to corresponding targets. Next, an "imager strand" is applied to the sample; this binds to the DNA-barcode of one of the targets. A coverslip is placed on the sample, and the imager strand is then detected using a fluorescence microscope. Next, the coverslip is removed; the sample is treated to remove the imager strand, and a second imager strand is applied to the sample; this binds to the second DNA-barcode. The second imager strand is then detected. The coverslip is again removed, and the sample treated to remove the second imager strand in preparation for round three. This process may be repeated to detect increasing numbers of biomarkers.

Thus, DNA Exchange Imaging requires application of new imager strands before each round of detection. Applying a collection of imager strands that would function effectively through multiple rounds of detection would reduce the amount of manipulation (and thus, time) required to complete an analysis. Such manipulation would be further reduced if coverslip removal could be avoided.

SUMMARY

In accordance with the description, methods and compositions for sequentially detecting targets in a sample are provided.

Accordingly, the following embodiments according to the methods and compositions described herein are provided.

Embodiment 1. A method for detecting a plurality of target molecules, the method comprising:
(a) contacting a sample with two or more target-specific binding partners, wherein each target-specific binding partner comprises a nucleic acid barcode; and is specific for a different target molecule;
(b) contacting the sample with one or more probe-sets wherein each probe in a probe-set is specific for a different target-specific binding partner, and wherein each probe-set comprises:
a first probe, comprising:
    a nucleic acid sequence complementary to a nucleic acid barcode of a corresponding target-specific binding partner;
    a first label; and
    a cleavage site for a first cleavage agent, wherein the first cleavage agent is capable of releasing the first label, and
a second probe comprising:
    a nucleic acid sequence complementary to a nucleic acid barcode of a corresponding target-specific binding partner;
    a second label;
    a quench moiety, wherein the quench moiety renders the second label undetectable; and
    a cleavage site for the first cleavage agent, wherein the first cleavage agent is capable of releasing the quench moiety, whereby the second label is rendered detectable; and optionally comprises a cleavage site for a second cleavage agent wherein the second cleavage agent is capable of releasing the second label;
(c) detecting signals corresponding to labels of the first probes of each of the one or more probe-sets;
(d) contacting the sample with a first cleavage agent, thereby releasing the labels of the first probes in each of the one or more probe-sets; and releasing the quench moieties of the second probes in each of the one or more probe-sets, thereby activating signals corresponding to the second labels, and
(e) detecting signals corresponding to the labels of the second probes of each of the one or more probe-sets.

Embodiment 2. The method of Embodiment 1, wherein one or more of the probe-sets further comprises a third probe, and the method further comprises:
(f) in step (b), contacting the sample with the third probe comprising:
a nucleic acid sequence complementary to a nucleic acid barcode of a corresponding target-specific binding partner;
a third label; and
a quench moiety, wherein the quench moiety renders the third label undetectable; and
a cleavage site for the second cleavage agent, wherein the second cleavage agent is capable of releasing the quench moiety, whereby the third label is rendered detectable;
and optionally comprises a distinct cleavage site for a distinct cleavage agent capable of releasing the third label; and
(g) after step (e), contacting the sample with a second cleavage agent, thereby releasing the labels of the second probes in each of the one or more probe-sets; and releasing the quench moieties of the third probes in one or more probe-sets, thereby activating signals corresponding to the third labels; and (h) detecting signals corresponding to the labels of the third probes of one or more probe sets.

Embodiment 3. The method of Embodiment 2, wherein one or more of the probe-sets further comprise a subsequent probe, and the method further comprises:

(i) in step (b), contacting the sample with a subsequent probe contained in one or more probe-set, wherein the subsequent probe comprises:
  a nucleic acid sequence complementary to a nucleic acid barcode of a corresponding target-specific binding partner;
  a subsequent label; and
  a quench moiety, wherein the quench moiety renders the subsequent label undetectable; and
  a cleavage site for a subsequent cleavage agent, wherein the subsequent cleavage agent is capable of releasing the quench moiety, whereby the subsequent label is rendered detectable;
  and optionally comprises a distinct cleavage site for a distinct cleavage agent capable of releasing activated labels from probes in the sample;
(j) contacting the sample with a subsequent cleavage agent, thereby releasing activated labels of the probes in each probe-set; and releasing the quench moieties of the subsequent probes in each probe-set, thereby activating signals corresponding to the labels of the subsequent probes in each probe-set; and
(k) detecting signals corresponding to the labels of the subsequent probes of each probe-set; and
(l) optionally repeating steps (i) through (k).

Embodiment 4. The method of Embodiment 1, wherein the first and second detectable labels of a probe-set are the same.

Embodiment 5. The method of Embodiment 1, wherein the first and second detectable labels of a probe-set are different.

Embodiment 6. The method of Embodiment 2, wherein the two or more of the first, second, and third detectable labels of a probe-set are the same.

Embodiment 7. The method of Embodiment 2, wherein the two or more of the first, second, and third detectable labels of a probe-set are different.

Embodiment 8. The method of Embodiment 3, wherein two or more of the first, second, third, and subsequent labels are the same.

Embodiment 9. The method of Embodiment 3, wherein two or more of the first, second, third, and subsequent labels are different.

Embodiment 10. The method of Embodiment 1, further comprising washing the sample after contacting the sample with the first cleavage agent and/or after contacting the sample with the second cleavage agent.

Embodiment 11. The method of Embodiment 1, wherein the sample is not washed after contacting the sample with the first cleavage agent and/or after contacting the sample with the second cleavage agent.

Embodiment 12. The method of Embodiment 11, wherein the coverslip is not removed.

Embodiment 13. The method of Embodiment 1, further comprising increasing the number of nucleic acid barcodes on a target-specific binding partner, wherein multiple copies of a corresponding probe bind to multiple copies of the nucleic acid barcode.

Embodiment 14. The method of Embodiment 13, wherein the number of nucleic acid bar codes is increased using rolling circle amplification, primer exchange reaction, hybridization chain reaction, or DNA branching.

Embodiment 15. The method of Embodiment 14, wherein the number of nucleic acid bar codes is increased before the target-specific binding partner is contacted with the sample.

Embodiment 16. The method of Embodiment 14, wherein the number of nucleic acid bar codes is increased when the target-specific binding partner is bound to its target molecule.

Embodiment 17. The method of Embodiment 1, wherein the released label of a first probe comprises a nucleotide sequence.

Embodiment 18. The method of Embodiment 17, further comprising contacting the sample with a background-reducing agent comprising a nucleotide sequence complementary to that of the released label of the released first probe, wherein binding of the background-reducing agent to the released label of the released first probe quenches the signal of the label.

Embodiment 19. The method of Embodiment 2, wherein the released label of a second probe comprises a nucleotide sequence.

Embodiment 20. The method of Embodiment 19, further comprising contacting the sample with a background-reducing agent comprising a nucleotide sequence complementary to that of the released label of the second probe, wherein binding of the background-reducing agent to the label of the released second probe quenches the signal of the label.

Embodiment 21. The method of Embodiment 3, wherein an activated label of a released probe comprises a nucleotide sequence.

Embodiment 22. The method of Embodiment 16, further comprising contacting the sample with a background-reducing agent comprising a nucleotide sequence complementary to that of the released label of the probe, wherein binding of the background-reducing agent to the released label of the released probe quenches the signal of the label.

Embodiment 23. A probe-set composition comprising:
one or more first probes, each comprising:
  a nucleic acid sequence complementary to a nucleic acid barcode of a corresponding target-specific binding partner;
  a first label; and
  a cleavage site for a first cleavage agent, wherein the first cleavage agent is capable of releasing the first label, and
one or more second probes, each comprising:
  a nucleic acid sequence complementary to a nucleic acid barcode of a corresponding target-specific binding partner;
  a second label;
  a quench moiety, wherein the quench moiety renders the second label undetectable; and
  a cleavage site for the first cleavage agent, wherein the first cleavage agent is capable of releasing the quench moiety, whereby the second label is rendered detectable;
  and optionally comprises a distinct cleavage site for a distinct cleavage agent capable of releasing the second label.

Embodiment 24. The composition of Embodiment 23, further comprising:
one or more third probes, each comprising:
  a nucleic acid sequence complementary to a nucleic acid barcode of a corresponding target-specific binding partner;
  a third label;
  a quench moiety, wherein the quench moiety renders the third label undetectable; and a cleavage site for a second cleavage agent, wherein the second cleavage agent is capable of releasing the quench moiety, whereby the third label is rendered detectable;

and optionally comprises a distinct cleavage site for a distinct cleavage agent capable of releasing the third label, wherein the second probe further comprises a cleavage site for the second cleavage agent.

Embodiment 25. The composition of Embodiment 24, further comprising:

a subsequent probe comprising:
- a nucleic acid sequence complementary to a nucleic acid barcode of a corresponding target-specific binding partner;
- a subsequent label;
- a quench moiety for the subsequent label, wherein the quench moiety renders the subsequent label undetectable; and
- a cleavage site, wherein a cleavage agent is capable of releasing the quench moiety, whereby the subsequent label is rendered detectable;
- and optionally comprises a distinct cleavage site wherein a distinct cleavage agent is capable of releasing the subsequent label, wherein another probe in the probe-set comprises a cleavage site for the same cleavage agent that releases the quench moiety of the subsequent probe.

Embodiment 26. The composition of Embodiment 23, wherein the one or more first probes have the same label.

Embodiment 27. The composition of Embodiment 23, wherein the one or more first probes have a different label.

Embodiment 28. The composition of Embodiment 23, wherein the cleavage site is an electromagnetic cleavage site; a chemical cleavage site; or a mechanical cleavage site.

Embodiment 29. The composition of Embodiment 28, wherein the electromagnetic cleavage site is a photocleavage site.

Embodiment 30. The composition of Embodiment 29, wherein the photocleavage site is an ultraviolet (UV) cleavage site.

Embodiment 31. The composition of Embodiment 23, wherein the first or second label is a fluorescent label.

Embodiment 32. The composition of Embodiment 23, further comprising: a background reducing agent comprising a nucleotide sequence complementary to a nucleotide sequence of a portion of a first probe present between the cleavage site and the first label.

Embodiment 33. The composition of Embodiment 32, further comprising: a background reducing agent comprising a nucleotide sequence complementary to a nucleotide sequence of a portion of a second probe present between the cleavage site and the second label.

Embodiment 34. The composition of Embodiment 33, further comprising: a background reducing agent comprising a nucleotide sequence complementary to a nucleotide sequence of a portion of a subsequent probe present between the cleavage site and the subsequent label.

Embodiment 35. A kit, comprising:
the probe-set composition of Embodiment 23;
a background-reducing agent;
a coverslip;
one or more target-specific binding partners;
one or more buffers;
one or more reagents for increasing the number of nucleic acid barcodes of a target-specific binding partner;
one or more cleavage agents;
a nuclear counterstain; and
instructions for use.

Embodiment 36. The kit of Embodiment 35, wherein the background-reducing agent is linked to a solid phase.

Embodiment 37. The kit of Embodiment 36, wherein the solid phase is selected from a coverslip; a particle and a slide.

Embodiment 38. The kit of Embodiment 35, wherein the background-reducing agent is in liquid phase.

Embodiment 39. A background reducing agent, comprising a nucleotide sequence complementary to a released label of a first probe of the composition of Embodiment 23, and a quench material.

Embodiment 40. A background reducing agent, comprising a nucleotide sequence complementary to a released label of a second probe of the composition of Embodiment 24, and a quench material.

Embodiment 41. A background reducing agent, comprising a nucleotide sequence complementary to a released activated label of a probe of the composition of Embodiment 25, and a quench material.

Embodiment 42. A method for detecting a plurality of target molecules, the method comprising:

(a) contacting a sample with two or more target-specific binding partners, wherein each target-specific binding partner comprises a nucleic acid barcode; and is specific for a different target molecule;

(b) contacting the sample with one or more probe-sets wherein each probe in a probe-set is specific for a different target-specific binding partner, and wherein each probe-set comprises:

a first probe, comprising:
- a nucleic acid sequence complementary to a nucleic acid barcode of a corresponding target-specific binding partner;
- a first label; and
- a cleavage site for a first cleavage agent, wherein the first cleavage agent is capable of suppressing the first label, and a second probe comprising:
- a nucleic acid sequence complementary to a nucleic acid barcode of a corresponding target-specific binding partner;
- a second label;
- a quench moiety, wherein the quench moiety renders the second label undetectable; and
- a cleavage site for the first cleavage agent, wherein the first cleavage agent is capable of releasing or suppressing the quench moiety, whereby the second label is rendered detectable;
- and optionally comprises a cleavage site wherein a second cleavage agent is capable of releasing or suppressing the second label;

(c) detecting signals corresponding to labels of the first probes of each of the one or more probe-sets;

(d) contacting the sample with a first cleavage agent, thereby suppressing the labels of the first probes in each of the one or more probe-sets; and releasing or suppressing the quench moieties of the second probes in each of the one or more probe-sets, thereby activating signals corresponding to the second labels; and (e) detecting signals corresponding to the labels of the second probes of each of the one or more probe-sets.

Embodiment 43. The method of Embodiment 42, wherein one or more of the probe-sets further comprises a third probe, comprising:

(f) in step (b), contacting the sample with a third probe contained in one or more probe-sets, wherein the third probe comprises:
  a nucleic acid sequence complementary to a nucleic acid barcode of a corresponding target-specific binding partner;
  a third label;
  a quench moiety, wherein the quench moiety renders the third label undetectable; and
  a cleavage site for a second cleavage agent, wherein the second cleavage agent is capable of releasing or suppressing the quench moiety, whereby the third label is rendered detectable;
  and optionally comprises a distinct cleavage site wherein a distinct cleavage agent is capable of releasing or suppressing the third label of one or more probe-sets; and
(g) after step (e), contacting the sample with a second cleavage agent, thereby suppressing the labels of the second probes in each of the one or more probe-sets; and releasing or suppressing the quench moieties of the third probes in one or more probe-sets, thereby activating signals corresponding to the third labels; and
(h) detecting signals corresponding to the third labels.

Embodiment 44. The method of Embodiment 43, wherein one or more of the probe-sets further comprise a subsequent probe, comprising:
(i) in step (b), contacting the sample with a subsequent probe contained in one or more probe-set, wherein the subsequent probe comprises:
  a nucleic acid sequence complementary to a nucleic acid barcode of a corresponding target-specific binding partner;
  a subsequent label; and
  a quench moiety, wherein the quench moiety renders the subsequent label undetectable; and
  a cleavage site, wherein a subsequent cleavage agent is capable of releasing or suppressing the quench moiety, whereby the subsequent label is rendered detectable;
  and optionally comprises a distinct cleavage site wherein a distinct cleavage agent is capable of suppressing activated labels from probes in the sample;
(j) contacting the sample with a subsequent cleavage agent, thereby suppressing activated labels of the probes in each probe-set; and releasing the quench moieties of the subsequent probes in each probe-set, thereby activating signals corresponding to the subsequent labels; and
(k) detecting signals corresponding to the subsequent labels; and
(l) optionally repeating steps (i) through (k).

BRIEF DESCRIPTION OF THE DRAWINGS

FIGS. 1A-D schematically depicts an exemplary probe-set of the present disclosure, containing a first probe (FIG. 1A); second probe (FIG. 1B), third probe (FIG. 1C); and fourth probe (FIG. 1D).

FIG. 2A schematically depicts three exemplary probe-sets (probe-sets A, B, and C) bound to nine target-specific binding partners (depicted as antibody-DNA conjugates). Probe-set A is directed to targets 1, 4 and 7. Probe-set B is directed to targets 2, 5 and 8. Probe-set C is directed to targets 3, 6 and 9. The exemplary probe-sets are designed for three rounds of detection: Round 1—targets 1, 2, and 3; Round 2—targets 4, 5 and 6; and Round 3,—targets 7, 8 and 9.

FIG. 2B schematically depicts the probe-sets bound to a prepared tissue sample fixed to a microscope slide, in accordance with an embodiment of the present disclosure. FIGS. 2C, 2D, and 2E schematically depict first, second, and third rounds of detection, respectively.

FIGS. 3A-C schematically depict an exemplary embodiment of a method described herein, where first, second and third probes of the probe-set depicted in FIG. 1 are bound to target-specific binding partners having multiple nucleic acid barcode repeats to which cognate probes bind (FIGS. 3A, 3B, and 3C, respectively).

FIGS. 4A-D schematically depict four exemplary cleavage modes useful in various embodiments of the present disclosure. FIG. 4A depicts use of ultraviolet (UV) light as a cleavage agent for a photocleavable bond. FIG. 4B depicts use of Tris(2-carboxyethyl)phosphine (TCEP) as a cleavage agent for a disulfide bond. FIG. 4C depicts use of a restriction enzyme as a cleavage agent for a specific nucleotide sequence. FIG. 4D depicts use of uracil-DNA glycosylase as a cleavage agent for a nucleic acid hairpin containing uracil-glycosidic bonds.

FIGS. 6A-B show fluorescence microscope images of a tissue sample processed according to an embodiment of the present disclosure, after a first round of detection of four targets (6A) and second round of detection of four different targets (6B).

FIGS. 11A-C show schematic depictions of designs of a background-reducing agent and images from rounds of detection using the background-reducing agent. FIG. 11A schematically depicts embodiments of designs of a background-reducing agent, a corresponding first probe (Probe design A) and a second probe (Probe design B). FIGS. 11B-C show images from two rounds of detection using the designs of FIG. 11A: a first round (FIG. 11B) in which CD8, PD1, PDL1 and CD68 were detected simultaneously; and a second round (FIG. 11C) in which CD3, CD4, FoxP3 and Cytokeratin were detected simultaneously, in accordance with the present disclosure.

FIGS. 12A-D shows images of detecting a target in tissue. The figures show images without coverslip removal, in the absence (FIGS. 12A/12B)) or presence (FIGS. 12C/12D)) of a background-reducing agent.

FIGS. 13A-B show schematics of exemplary probe sets and images generated from reactions using those probe sets. Specifically, FIG. 13A schematically depicts an exemplary probe-set containing four members, designed for four rounds of detection using three different cleavage agents (TCEP, UV photocleavage; and uracil-DNA-glycosylase).

FIG. 13B shows images of sixteen detected target molecules using four probe-sets according to the probe-set embodiment shown in FIG. 13A.

DESCRIPTION

Figure 2A:
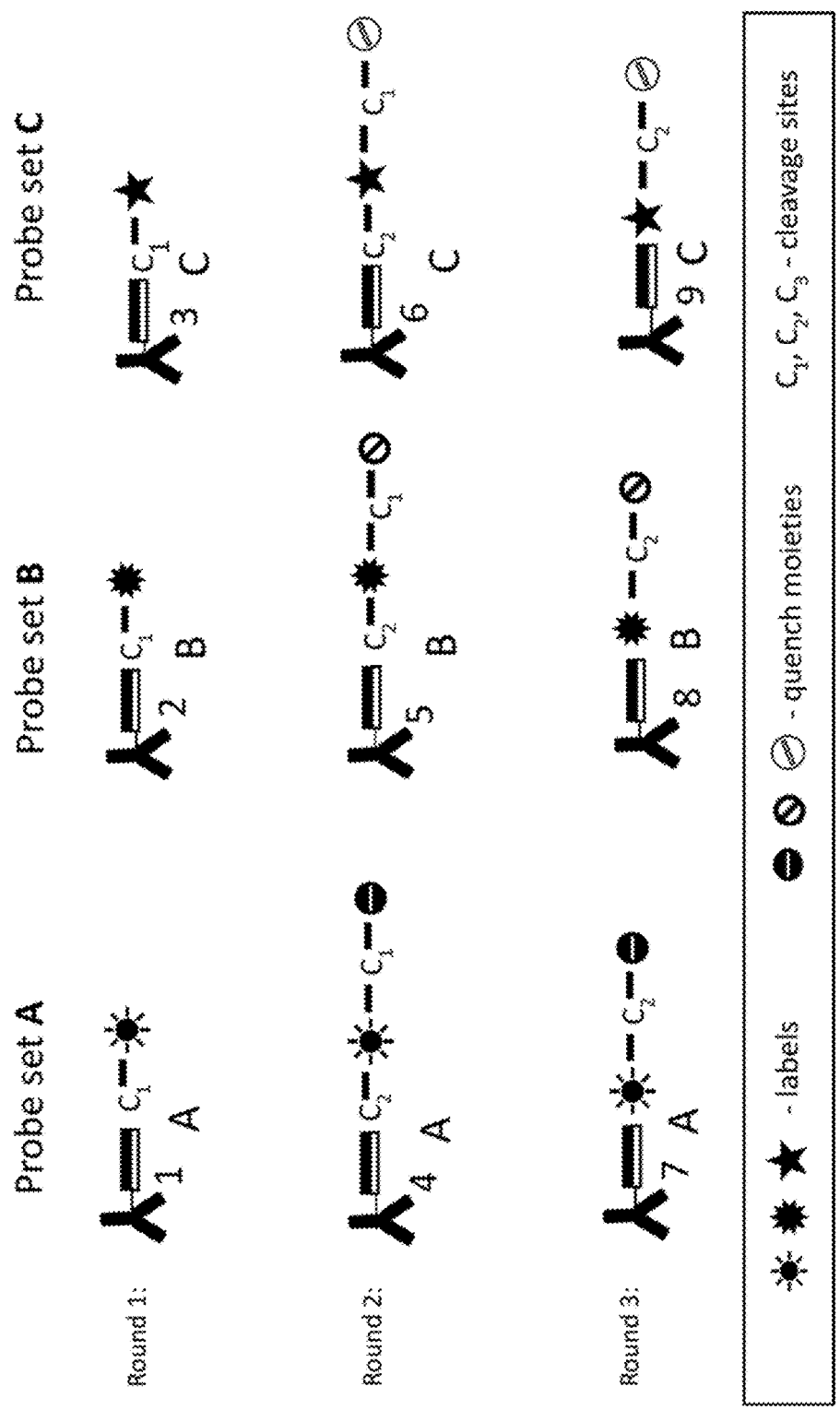
FIGS. 2A-E provide schematics of embodiments disclosed herein.

Described herein are probe-sets for multiplex detection of target molecules (or "targets"), related methods and kits for using them, and related background-reducing agents. In an embodiment, the methods can be used to detect multiple target molecules with a single up-front application of target-binding partners and labeled probes, followed by sequential detection of subpopulations of probes. In various embodiments, a multiplex method can be implemented without direct access to the sample after initial application of probes, for example, without removing a coverslip enclosing a tissue sample.

Although embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the embodiments, specific terminology will be resorted to for the sake of clarity.

It must also be noted that, as used in the specification and the appended claims, the singular forms "a," "an" and "the" include plural referents unless the context clearly dictates otherwise. For example, reference to a sheet or portion is intended also to include the manufacturing of a plurality of sheets or portions. References to a sheet containing "a" constituent is intended to include other constituents in addition to the one named.

Also, in describing the embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a fabric or system does not preclude the presence of additional components or intervening components between those components expressly identified.

Methods for multiplexed detection of targets in tissue samples using fluorescence microscopy have been described, for example, in U.S. Pat. No. 9,944,972 and are commercially available. The InSituPlex multiplex detection technology (Ultivue, Inc.) is used for detecting multiple targets as follows. First, a collection of DNA-barcoded antibodies for four targets are applied to the sample, where the DNA-barcodes are distinct for each antibody. After amplification of the DNA-barcodes, fluorescently labeled probes that bind to the barcodes are applied. The fluorescent labels are spectrally distinct and all can be imaged simultaneously. Additional targets may be examined by removing the probes, and applying another collection of probes complementary to a second set of barcoded antibodies. Thus, in an assay designed to examine nine targets using this method, the user could image the first three targets then perform exchange by removing the probes and applying the next round of three probes. Targets four through six would then be imaged, and exchange would again be performed. Targets seven through nine would then be imaged.

In contrast, the methods described herein employ probe-sets that can be simultaneously applied to a sample, and sequentially detected without the need for an exchange step. FIGS. 1A-D (depicting Probes A, B, C, and D, respectively) schematically depict an exemplary probe-set of the present disclosure. Although a variety of variations are possible, this figure shows a basic implementation of the present disclosure. In this embodiment, each probe (A, B, C, and D) is specific for a different target, and each contains the same label. Probes B, C, and D contain the same quench moiety, which is capable of quenching the label. Probes A and B contain a common cleavage site ($C_1$), which permits simultaneous release of the label of Probe A, and de-quenching of the label of Probe B. Probes B and C contain a common cleavage site ($C_2$), which likewise permits simultaneous release of the label of Probe B, and de-quenching of the label of Probe C. Probes C and D contain a common cleavage site ($C_3$), which permits simultaneous release of the label of Probe C, and de-quenching of the label of Probe D. Probe D optionally contains a cleavage site ($C_4$), which permits release of the label of Probe D, and optionally, de-quenching of the label of a subsequent probe.

Figure 2B:
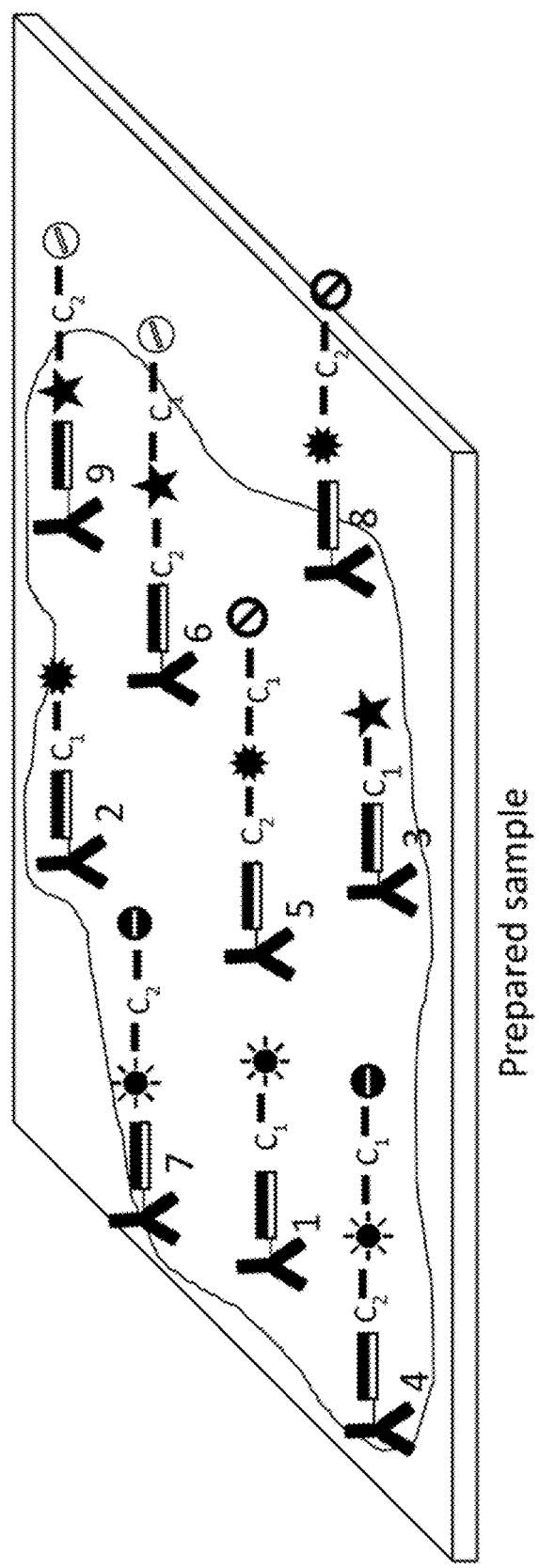

FIG. 2A schematically depicts three exemplary probe-sets bound to target-specific binding partners (TSBPs) in accordance with the present disclosure. In this embodiment, nine different targets are detected using three rounds of detection, with members of probe-sets A, B, and C used in each round. TSBPs are depicted as antibodies having nucleic acid segments, each having a distinct barcode to which a distinct probe binds. The probes of each probe-set are depicted as bound to their matching TSBPs. The probes within a particular probe-set contain a common label (see FIG. 2A legend). Each different probe-set has a different label and corresponding quench moiety in this embodiment. FIG. 2B schematically depicts the exemplary probe-bound TSBPs of FIG. 2A when bound to targets of a tissue sample on a slide.

Figure 2C:
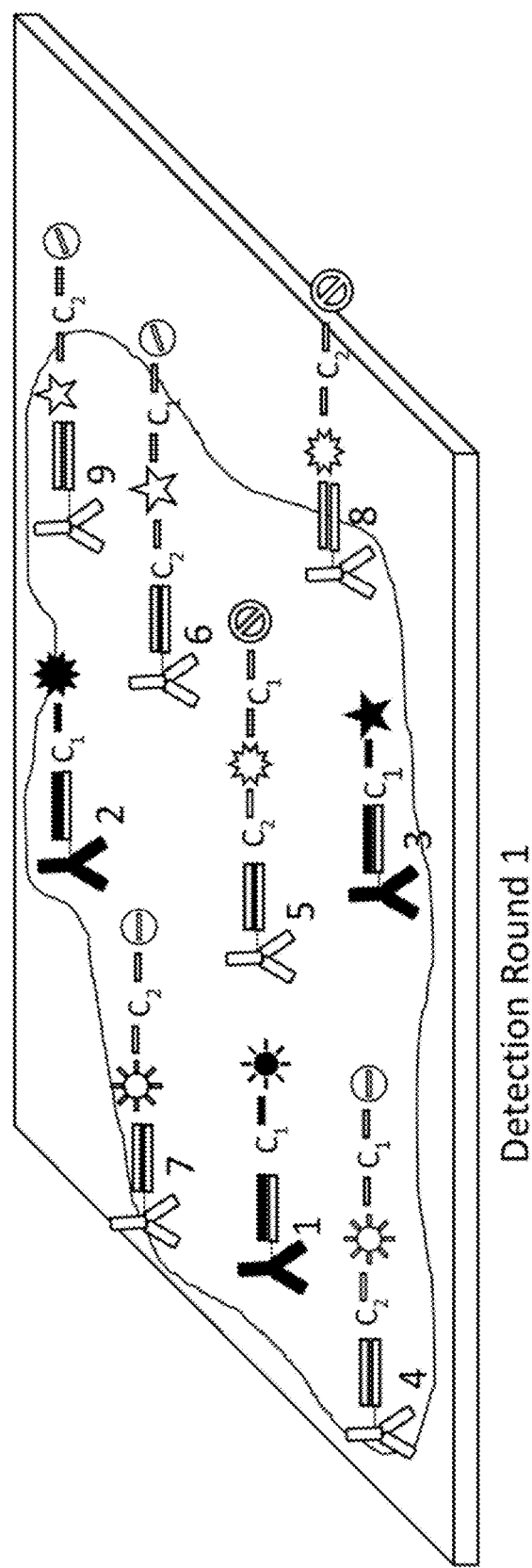

FIG. 2C schematically depicts Round 1 of detection, where in this embodiment, the labels of the first probes (targets 1, 2 and 3) of each probe-set are detected. The detectable probes are depicted as black probe/TSBP/target complexes; the non-detectable probes are depicted in grey probe/TSBP/target complexes.

Figure 2D:
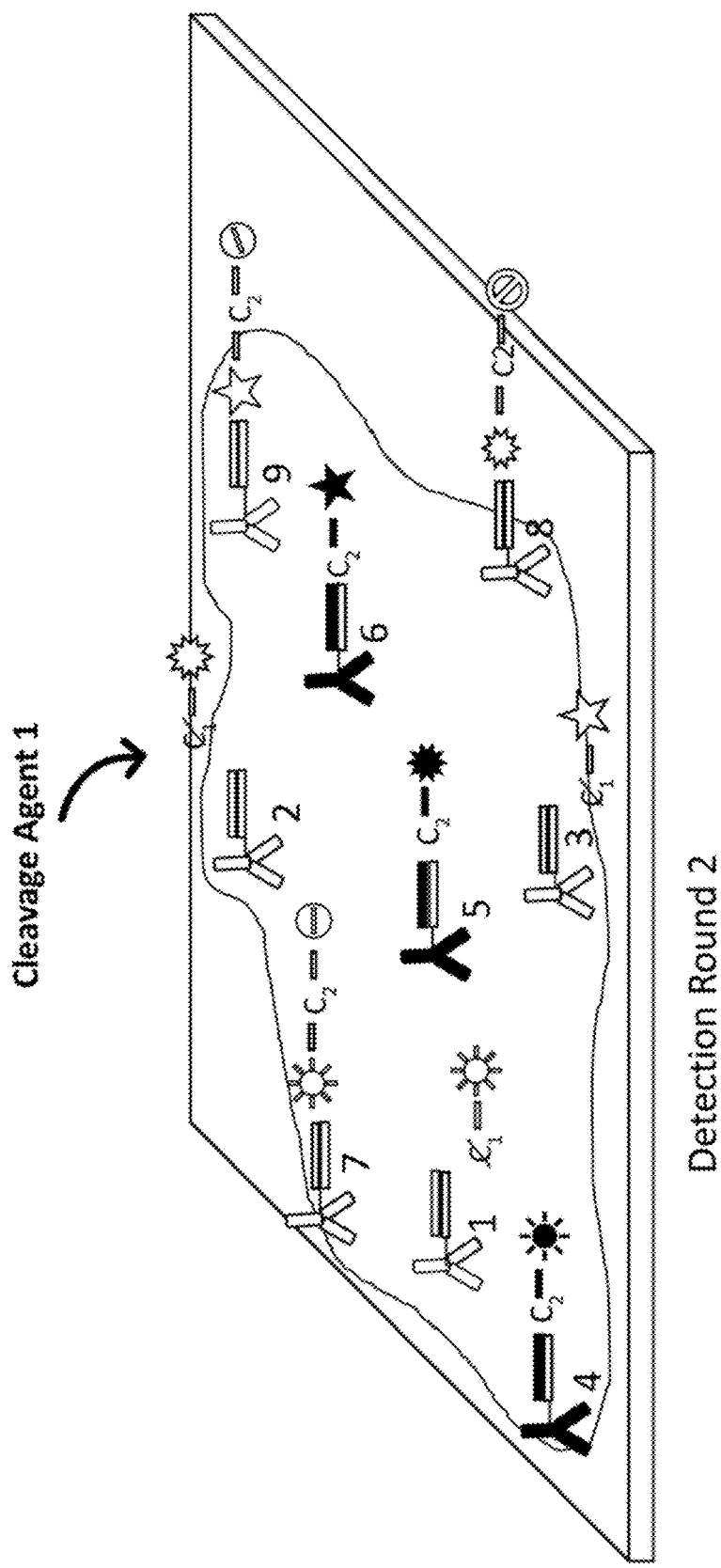

FIG. 2D schematically depicts Round 2 of detection, which is preceded by application of a cleavage agent that releases the labels of the first probes of each probe-set and releases the quench moiety of the second probes of each probe-set. Release of the quench moieties renders the labels of the second probes of each probe-set detectable, and release of the labels of the first probes removes their signals from the TSBP/target complexes. Accordingly, the now-detectable second probes (targets 4, 5 and 6) of each probe-set are depicted as black probe/TSBP/target complexes.

Figure 2E:
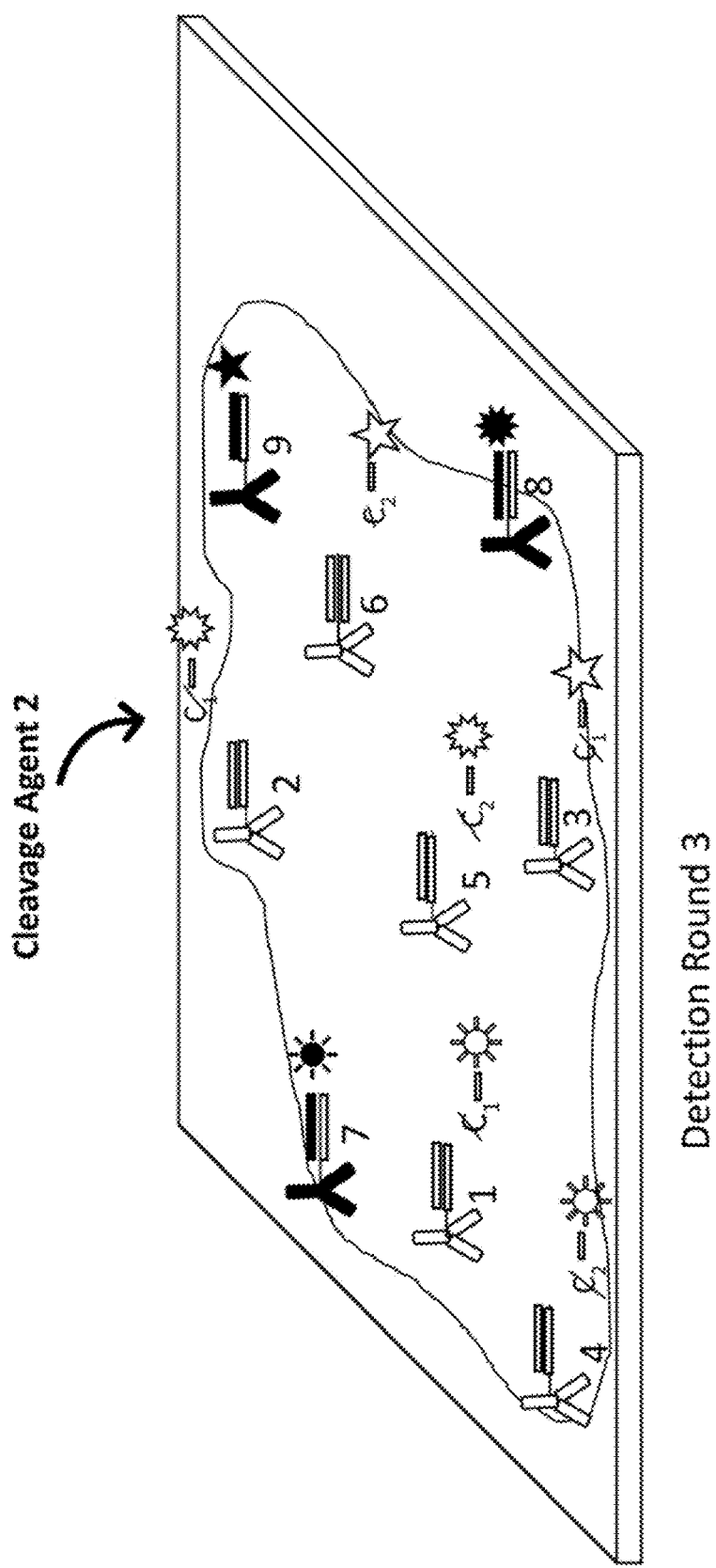

FIG. 2E schematically depicts Round 3 of detection, which is preceded by application of a second cleavage agent that releases the labels of the second probes of each probe-set and releases the quench moiety of the third probes of each probe-set. Accordingly, the now-detectable third probes (targets 7, 8 and 9) of each probe-set are depicted as black probe/TSPB/target complexes. A label cleavage site may be present or absent from a probe used in a final round of detection because a user may or may not desire to remove the last-detected signal.

FIGS. 3A-3C schematically depict an exemplary embodiment of a method described herein, where first, second and third probes of the probe-set are bound to TSBP, where each TSBP contains multiple identical nucleic acid barcode repeats to which cognate probes bind. Binding of multiple probes to each TSBP is an exemplary method for amplifying the detectable signals of the probes.

FIGS. 4A-4D schematically depict four exemplary cleavage modes useful in various embodiments of the present disclosure. In FIG. 4A, the quenched label of a probe bound to a TSPB/target is activated when UV light is used as a cleavage agent for a photocleavable bond. In FIG. 4B, the quenched label is activated when Tris(2-carboxyethyl)phosphine (TCEP) is used as a cleavage agent for a disulfide bond. In FIG. 4C, the quenched label is activated when a restriction enzyme is used as a cleavage agent for a specific nucleotide sequence. In FIG. 4D, the quenched label is activated when uracil-DNA glycosylase is used as a cleavage agent that hydrolyzes uracil-glycosidic (UA) bonds, destabilizing a DNA duplex.

Figures 5A, 5B, 5C, 5D:
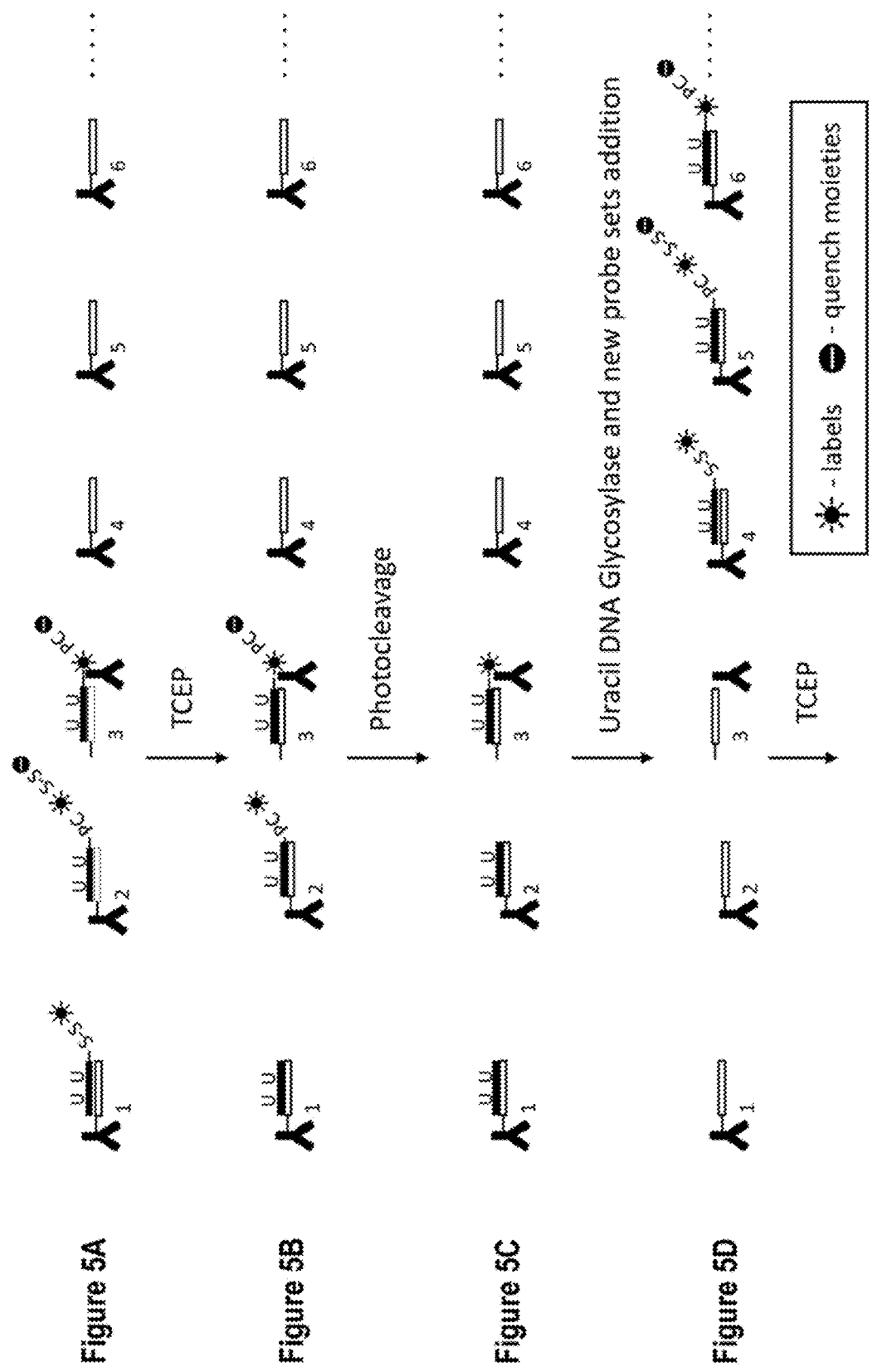
FIGS. 5A-D schematically depict an exemplary embodiment of the present disclosure in which three targets are detected after application of three probes of a probe-set, using three rounds of detection; and then new probes are applied to the sample and subsequent rounds of detection are performed.

FIGS. 5A-5B schematically depict an exemplary embodiment of the described methods, which illustrates that serial probe-sets may be used to detect increasing numbers of targets. The illustration depicts that a first target is detected in round A (FIG. 5A); the sample is treated with TCEP to release the first label and unquench the second label; a second target is detected in round B (FIG. 5B); the sample is then treated with UV light to release the second label and unquench the third label; a third target is detected in round C (FIG. 5C); the sample is next treated with uracil DNA glycosylase to release the third label; another probe-set is added to the sample, and a fourth target is detected in round D (FIG. 5D); the user continues with one or more rounds of detection using any selected cleavage modes to detect additional targets. Other types of probes also may be used with the probe-set described herein to detect additional targets.

Therefore, the present disclosure provides compositions, kits and methods for detecting a plurality of targets. Provided herein is a probe-set composition. The composition includes one or more first probes, each containing a nucleic acid sequence complementary to a nucleic acid barcode of a corresponding target-specific binding partner; a first label; and a cleavage site for a first cleavage agent, wherein the first cleavage agent is capable of releasing the first label, and one or more second probes, each containing nucleic acid sequence complementary to a nucleic acid barcode of a corresponding target-specific binding partner; a second label; a quench moiety, wherein the quench moiety renders the second label undetectable; and a cleavage site for the first cleavage agent, wherein the first cleavage agent is capable of releasing the quench moiety, whereby the second label is rendered detectable; and optionally comprises a distinct cleavage site for a distinct cleavage agent capable of releasing the second label.

In some embodiments, a probe-set can further include one or more third probes, each comprising: a nucleic acid sequence complementary to a nucleic acid barcode of a corresponding target-specific binding partner; a third label; a quench moiety, wherein the quench moiety renders the third label undetectable; and a cleavage site for a second cleavage agent, wherein the second cleavage agent is capable of releasing the quench moiety, whereby the third label is rendered detectable; and optionally comprises a distinct cleavage site for a distinct cleavage agent capable of releasing the third label, wherein the second probe further comprises a cleavage site for the second cleavage agent.

In some embodiments, a probe-set can be expanded to include a subsequent probe comprising: a nucleic acid sequence complementary to a nucleic acid barcode of a corresponding target-specific binding partner; a subsequent label; a quench moiety for the subsequent label, wherein the quench moiety renders the subsequent label undetectable; and a cleavage site, wherein a cleavage agent is capable of releasing the quench moiety, whereby the subsequent label is rendered detectable; and optionally comprises a distinct cleavage site wherein a distinct cleavage agent is capable of releasing the subsequent label, wherein another probe in the probe-set comprises a cleavage site for the same cleavage agent that releases the quench moiety of the subsequent probe.

The term "first probe" means a probe that contains at least (1) a nucleic acid sequence complementary to a nucleic acid barcode of a corresponding target-specific binding partner; (2) a first label; and (3) a cleavage site for a first cleavage agent, wherein the first cleavage agent is capable of releasing the first label. A first probe can further contain one or more additional quench moieties, one or more other labels, and one or more other cleavage sites that are deployed or undeployed in a method step. Elements that remain undeployed in a particular method (e.g., a photocleavage site is present when no photocleavage agent is employed in the method) can be used in alternative methods, giving the user flexibility when designing assay flows. A probe may have more than one cleavage site for the same cleavage agent, or distinct cleavage sites for distinct cleavage agents that do not interfere with subsequent steps. Such redundancies may be useful, for example, for weaker cleavage agents, to create shorter released probe fragments, or other purposes. Similarly, a second, third, and subsequent probe can contain any number of quench moieties, labels, and/or cleavage sites. Therefore, in some embodiments, some probes of a probe-set may contain one or more labels, quench moieties, or cleavage sites that are not deployed. In some embodiments, the cleavage product of a probe may contain more than one label, quench moiety, and/or undeployed cleavage site. It is foreseeable that cleavage of a probe can release more than one cleavage product. If desired, a first probe can contain a quench moiety such that a cleavage agent is contacted with a sample prior to detecting the label of a first probe.

If desired, two or more probes can be designed to produce a proximity signal that reflects the physical distance between two or more targets using fluorescence resonance energy transfer (FRET). In an embodiment of this implementation, a probe contains a label (e.g., fluorophore) that is capable of being quenched by a label (e.g., quencher) contained on another probe, when the probes are bound to targets in close proximity. Therefore, a FRET signal of a donor or acceptor label can be detected in one or more rounds of detection as described herein.

Figure 8B:
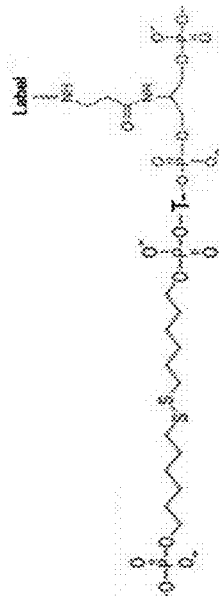
FIGS. 8A-D shows segments of exemplary probes of the present disclosure.
Figure 8D:
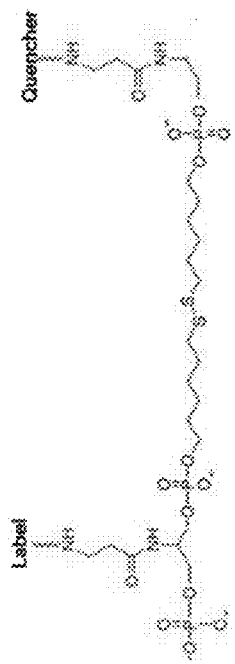
Figure 8A:
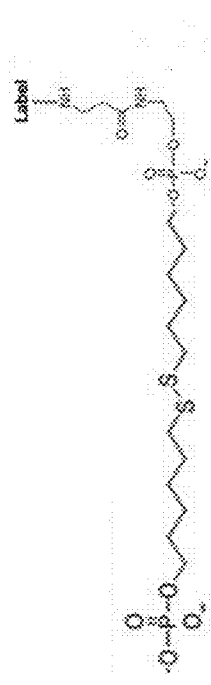
Figure 8C:
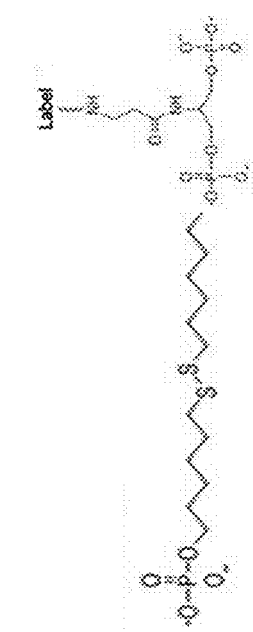

FIGS. 8A-8D depict segments of exemplary probes encompassed by the present disclosure. FIGS. 8A-8C show exemplary first probe segments containing a disulfide cleavage site and a terminal label. The number of nucleotides, or physical distance imparted by other chemistry, can vary as selected by the user. In FIG. 8B, 'T' is a thymine base. FIG. 8D shows an exemplary second probe segment containing a disulfide cleavage site between a label and a quench moiety.

It may be desired to reduce the signal from labels released from probes prior to detecting the labels of the next-to-be-detected probes. A background-reducing agent can be employed for this purpose. As used herein, the term "background-reducing agent" means a material that binds to a released label of a probe and reduces the label's signal, which otherwise could produce unwanted or background signal. A background-reducing agent can reduce signal by one or more mechanisms, including direct or indirect quenching of the label; relocation of the label outside of a selected imaging field; or both. A background-reducing agent can bind non-selectively or selectively to a released label.

Figure 9:
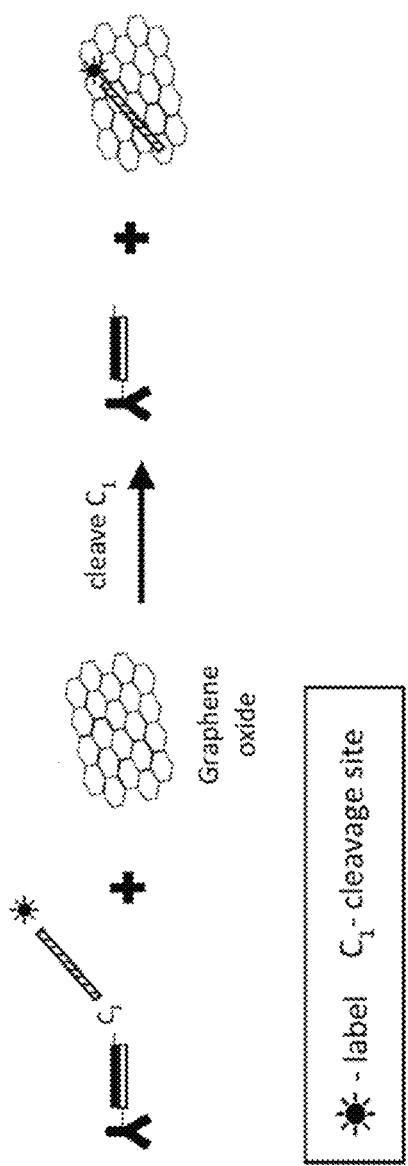
FIG. 9 schematically depicts an exemplary non-selective background-reducing agent.

In an embodiment, a non-selective background-reducing agent is a carbon nanoparticle carbon nanomaterial including macroscopic, mesoscopic, and nanoscale materials, including single crystal carbon, carbon sheets, glassy carbon, carbon black, carbon pastes, activated carbon, graphene, carbon nanotubes, graphene oxide, and carbon dots. Exemplary size ranges for particles include one dimension less than 20 nm. Graphene oxide particles possess hydroxyl and carboxyl groups in addition to graphenic carbon. While the carboxyl groups impart ionicity that favors solubility in aqueous solutions, the high degree of charge on the particles promotes surface adsorption as well. Thus, useful carbon nanoparticles may exhibit a high degree of hydroxyls relative to carboxyls. Graphene oxide has been used, for example, to reduce unwanted fluorescence in tissue microscopy (see, for example, Li, R., Georgiades, P., Cox, H. et al. Quenched Stochastic Optical Reconstruction Microscopy (qSTORM) with Graphene Oxide. Sci Rep 8, 16928 (2018) doi:10.1038/s41598-018-35297-4). As depicted in FIG. 9, a released label can bind to graphene oxide, which can be in solution or attached to a solid support (e.g. a coverslip, slide or particle), and subsequently signal from the released label is suppressed or quenched.

In an embodiment, a selective background-reducing agent binds specifically to a nucleotide sequence contained in a released label. In an embodiment, such a selective background-reducing agent binds to the released label, resulting in quenching of the label when a quencher of the background-reducing agent is brought into proximity with the label. This is useful, for example, when performing a cleavage without removal of the coverslip, such as the UV photocleavage embodiments described herein.

Therefore, in an embodiment, a nucleic acid selective background-reducing agent is a molecule or complex comprising (i) a nucleotide sequence complementary to a nucleotide sequence contained in a probe segment comprising a label, which is released from a probe upon cleavage by a cleavage agent; (ii) a quencher capable of quenching the signal of the label; and optionally (iii) a cleavage site whereby the background-reducing agent is itself activated or made available for interacting with the probe segment (e.g., in the case of a caged background-reducing agent) or released from a solid support (e.g., in the case of release from a coverslip, microscope slide, bead and the like).

Figure 10:
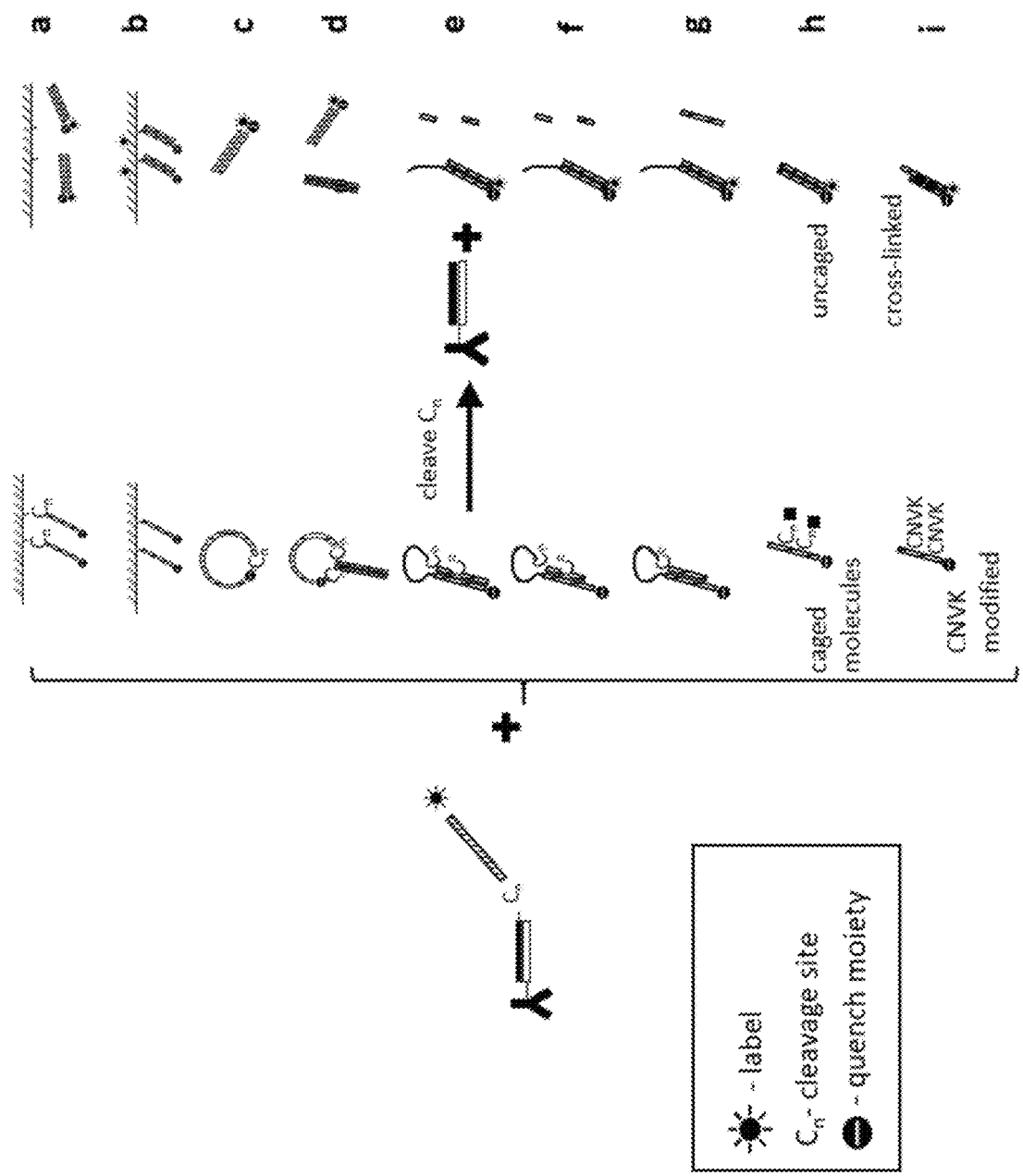
FIG. 10 schematically depicts exemplary embodiments of selective background-reducing agents.

In some embodiments, the background-reducing agent is linked to a solid support, such as a sample enclosure (e.g., a coverslip, slide, capillary) or accessory (e.g., bead, particle). When a solid support is used, the background-reducing agent can remain associated with the support and thereby attract released labels to the support. Alternatively, the background-reducing agent can be liberated from the support by a cleavage agent, which can be the same as the cleavage agent used to release its partner released label, or a different cleavage agent. FIG. 10 shows background-reducing agent initially attached to a support and subsequently cleaved from the support and bound to released labels (e.g., FIG. 10, *a*); and background-reducing agent that remains attached to a support when bound to released labels (e.g., FIG. 10, *b*).

A background-reducing agent can have a variety of structures. In an embodiment, a background-reducing agent comprises a circularized nucleic acid. A circularized nucleic acid may include a cleavage site whereby cleavage renders the background-reducing agent available for interacting with its partner released label (e.g., FIG. 10, *c*). In an embodiment, a background-reducing agent comprises a nucleic acid hairpin structure (e.g., FIG. 10, *d*). In some embodiments, a background-reducing agent comprises a nucleic acid hairpin structure comprising one or more cleavage sites whereby cleavage renders the background-reducing agent available for interacting with its partner released label (e.g., FIG. 10, *e, f, g*).

In an embodiment, a background-reducing agent comprises a cleavage site whereby cleavage renders the agent activated or available for interacting with its partner released label. Cleavage sites and cleavage agents are described herein below; any of a variety of such cleavage sites and cleavage agents are suitable for use in a background-reducing agent. In some embodiments, a background-reducing agent comprising caged molecules that block interaction with partner released labels, until a cleavage agent is used to uncage the blockers, allowing the agent to interact with its partner released label (e.g., FIG. 10, *h*).

The interaction between a background-reducing agent and its partner released label can be non-covalent or covalent. Exemplary non-covalent interactions include binding between complementary or partially complementary nucleic acids. Exemplary covalent interactions include cross-linking between complementary or partially complementary nucleic acids (e.g., FIG. 10, *i*; 3-cyanovinylcarbazole nucleoside photocrosslinker (CNVK)). Thus, a background-reducing agent may be capable of cross-linking to a released label. This can be useful when using a relatively lower affinity binding site for a released label, such as a nucleic acid sequence that binds transiently under the assay conditions employed.

Any cleavage agent described herein can be used for a background-reducing agent. In a specific embodiment, a background-reducing agent can be activated by a photocleavage agent. As described in Example 7 below, when a photocleavage agent is used in a fluorescence microscopy method, the sample can be treated with a photocleavage wavelength of light (e.g., 385 nm) using the imaging system without removal from the stage used for acquiring a first (or subsequent) round of images. Alternatively, the sample can be removed from the imaging system; externally treated with the photocleavage agent; and returned to the imaging system (or another detection mode) for a next detection round. As described elsewhere in this disclosure, images from different rounds can be aligned using well known methods.

A composition containing a background-reducing agent can be provided in any form, such as dried, solubilized in a compatible liquid, in a colloidal mixture, and together with other components, for example, for convenience of a particular workflow. As such, a background-reducing agent can be a component of a background-reducing mounting medium.

A background-reducing mounting medium is a fluid to be disposed between a tissue and a coverslip, which includes one or more quenchers selective for one or more labels. The fluid can contain one or more of, or a combination of: salts, buffers, hardening agents, anti-fade agents, and staining reagents (e.g., a nuclear counterstain). Examples of commercial mounting reagents that can be used as a base for adding a background-reducing agent include Prolong Gold Anti-Fade Mountant (ThermoFisher); and Vectashield (Vecta Laboratories). Examples of common reagents that can be used as a base for adding affinity and/or quench materials include a variety of buffers used for biological samples such as phosphate buffered saline (PBS) and tris (hydroxymethyl)aminomethane (Tris)-based buffers.

The present disclosure provides kits for multiplex detection of a plurality of target molecules. In an embodiment, a kit includes one or more probe-sets as described herein together with one or more other components. Each probe-set includes one or more first probes and one or more second probes. Optionally one or more third probes; fourth probes, fifth probes; sixth probes, or more probes can be included. The one or more other kit components can include one or more of instructions for use; one or more background-reducing agents; one or more cleavage agents; one or more target-specific binding partners; one or more buffers; one or more reagents for increasing the number of nucleic acid barcodes of a target-specific binding partner; a nuclear counterstain; a background-reducing mounting medium; a coverslip; plate; control sample; software; and other component.

The present disclosure provides methods for detecting a plurality of target molecules. In an embodiment, the method involves: (a) contacting a sample with two or more target-specific binding partners, wherein each target-specific binding partner comprises a nucleic acid barcode; and is specific for a different target molecule; (b) contacting the sample with one or more probe-sets wherein each probe in a probe-set is specific for a different target-specific binding partner, and wherein each probe-set comprises a first probe, comprising a nucleic acid sequence complementary to a nucleic acid barcode of a corresponding target-specific binding partner; a first label; and a cleavage site for a first cleavage agent, wherein the first cleavage agent is capable of releasing the first label, and a second probe comprising a nucleic acid sequence complementary to a nucleic acid barcode of a corresponding target-specific binding partner; a second label; a quench moiety, wherein the quench moiety renders the second label undetectable; and a cleavage site for a first cleavage agent, wherein the first cleavage agent is capable of releasing the quench moiety, whereby the second label is rendered detectable; and optionally comprises a cleavage site for a second cleavage agent, wherein the second cleavage agent is capable of releasing the second label; (c) detecting signals corresponding to labels of the first probes of each probe-set; (d) contacting the sample with a first cleavage agent, thereby releasing the labels of the first probes in each probe-set; and releasing the quench moieties of the second probes in each probe-set, thereby activating signals corresponding to the second labels of the second probes in each probe-set; and (e) detecting signals corresponding to the labels of the second probes of each probe-set.

In some embodiments, one or more of the probe-sets further comprises a third probe and the method described herein involves, at step (b), contacting the sample with the third probe containing a nucleic acid sequence complementary to a nucleic acid barcode of a corresponding target-specific binding partner; a third label; and a quench moiety, wherein the quench moiety renders the third label undetectable; and a cleavage site for the second cleavage agent, wherein the second cleavage agent is capable of releasing the quench moiety, whereby the third label is rendered detectable; and optionally comprises a distinct cleavage site for a distinct cleavage agent capable of releasing the third label of one or more probe-sets; and the method further comprises, after step (e), contacting the sample with a second cleavage agent, thereby releasing the labels of the second probes in each of the one or more probe-sets; and releasing the quench moieties of the third probes in one or more probe-sets, thereby activating signals corresponding to the labels of the one or more third probes; and detecting signals corresponding to the labels of the one or more third probes.

In an embodiment, the method described herein involves use of one or more of the probe-sets containing a subsequent probe. The method involves, (i) in step (b), contacting the sample with a subsequent probe contained in one or more probe-set, wherein the subsequent probe comprises: a nucleic acid sequence complementary to a nucleic acid barcode of a corresponding target-specific binding partner; a subsequent label; and a quench moiety, wherein the quench moiety renders the subsequent label undetectable; and a cleavage site for a subsequent cleavage agent, wherein a subsequent cleavage agent is capable of releasing the quench moiety, whereby the subsequent label is rendered detectable; and optionally comprises a distinct cleavage site wherein a distinct cleavage agent is capable of releasing activated labels from probes in the sample; (j) contacting the sample with a subsequent cleavage agent, thereby releasing activated labels of the probes in each probe-set; and releasing the quench moieties of the subsequent probes in each probe-set, thereby activating signals corresponding to the labels of the subsequent probes in each probe-set; and (k) detecting signals corresponding to the labels of the subsequent probes of each probe-set; and (l) optionally repeating steps (i) through (k).

The method can further include, in step (b), contacting the sample with two or more probe-sets, herein each probe-set further comprises a subsequent probe, comprising: a nucleic acid sequence complementary to a nucleic acid barcode of a corresponding target-specific binding partner; a subsequent label; and a quench moiety, wherein the quench moiety renders the subsequent label undetectable; and a cleavage site, wherein a subsequent cleavage agent is capable of releasing the quench moiety, whereby the subsequent label is rendered detectable; and optionally comprises a distinct cleavage site wherein a distinct cleavage agent is capable of releasing the an activated label from probes in the sample; (j) after step (h), contacting the sample with a subsequent cleavage agent, thereby releasing activated labels of the probes in each probe-set; and releasing the quench moieties of the subsequent probes in each probe-set, thereby activating signals corresponding to the labels of the subsequent probes in each probe-set; and (k) detecting signals corresponding to the labels of the subsequent probes of each probe-set; and (l) optionally repeating steps (i) through (k).

In various embodiments, the first and second detectable labels can be the same; the first, second, and third detectable labels can be the same; and the first, second, third and subsequent detectable labels can be the same. Because the first, second, third, and subsequent detectable labels in a probe-set are detected in first, second, third, and subsequent rounds of detection, the labels need not be different (but can be different). However, the first, second, third, and subsequent detectable labels of one probe-set are different from those of a different probe-set, when detected in a first, second, third, and subsequent round of detection.

When multiple probe-sets are used in a fluorescence detection mode, it can be convenient to detect all first probes using the same detection channel. For example, when all labels are FITC-like, detection in a single detection channel is possible. It is not necessary that all probes contain the same detectable label for them to be detected in the same detection channel, as a variety of fluorescent dyes are detectable in the same detection channel, as described in more detail below. Detection in more than one detection channel in a single round, as well as more than one detection mode, can be used.

In various embodiments, the method can involve increasing the number of nucleic acid barcodes contained in a TSBP, wherein multiple copies of a corresponding probe bind to multiple copies of the nucleic acid barcode. The number of barcodes can be increased using a method such as PCR, rolling circle amplification, primer exchange reaction (PER), HCR, branched amplification, or a combination of two or more methods. The method can be performed prior to addition of the target-specific binding partner to the sample, or after the target-specific binding partner is contacted with the sample.

In some embodiments, the target may be a polypeptide or a nucleic acid. Accordingly, a target-specific binding partner can contain a target-binding functionality that recognizes a polypeptide, nucleic acid, or other target.

In some embodiments, the cleavage site may be a chemical cleavage site; a mechanical cleavage site; an electromagnetic cleavage site, such as a photocleavage site; or an enzymatic cleavage site.

In some embodiments, the label is a fluorescent label. As described below, multiple fluorescent labels can be simultaneously selected using routine methods.

In various embodiments of the described methods, the sample can be washed after contact with a cleavage agent. This is useful when the released label retains sufficient signal to produce unwanted background signal.

In some embodiments, the sample is not washed after contact with a cleavage agent. This is useful when performing the method on a tissue sample covered by a coverslip, when it is desired to not remove the coverslip.

In some embodiments the released label of a first probe comprises a nucleotide sequence. In such embodiments, a method can further comprise contacting the sample with a background-reducing agent comprising a nucleotide sequence complementary to that of the released label of the released first probe, wherein binding of the background-reducing agent to the released label of the released first probe quenches the signal of the released first label.

Similarly, in some embodiments the released label of a second probe comprises a nucleotide sequence. In such embodiments, a method can further comprise contacting the sample with a background-reducing agent comprising a nucleotide sequence complementary to that of the released label of the second probe, wherein binding of the background-reducing agent to the label of the released second probe quenches the signal of the released second label.

Likewise, in some embodiments, an activated label of a released probe comprises a nucleotide sequence. In such embodiments, a method can further comprise contacting the sample with a background-reducing agent comprising a nucleotide sequence complementary to that of the released label of the probe, wherein binding of the background-reducing agent to the released label of the released probe quenches the signal of the label.

The methods and compositions described herein can be used to detect a variety of types of targets. Exemplary types of targets include macromolecules such as proteins, carbohydrates, lipids, and nucleic acids (e.g., DNA, RNA, short interfering nucleic acid (siNA), and short interfering RNA (siRNA)); and small molecules such as primary metabolites, secondary metabolites, and natural products. A target can be naturally occurring, in that it is present in organisms or viruses that exist in nature in the absence of human intervention, or can be synthetic. The methods and compositions can be used to detect any target for which a target-specific binding partner exists.

Therefore, in some embodiments, a target is a protein. Examples of protein targets include cytoplasmic, nuclear, membrane, and non-cellular proteins, such as structural proteins (e.g. actin, vimentin, dystrophin, keratin); extracellular matrix proteins (e.g. elastin, fibronectin); cellular receptors (e.g. epidermal growth factor receptor, nerve growth factor receptor, estrogen receptor); ion channels (e.g. GABA receptor, nicotinic acetylcholine receptor); hormones (e.g. insulin, oxytocin, androgens); DNA-binding proteins (e.g. P53, histones); immune system proteins (e.g. CD3, CD4, CD8, CD20, CH11c, CD25, CD45RO, CD68, CD163, granzyme B, FoxP3, LAG3, MCHII, PD1, and PDL-1); and any other protein of interest.

In some embodiments, a target is a nucleic acid molecule. Examples of nucleic acid molecule targets include DNA and RNA. Example 5 below describes an embodiment in which miRNA targets are detected.

As used herein, a "target-specific binding partner" means a molecule (or complex of molecules) that both (1) binds selectively to a target and (2) binds selectively to a probe. As such, a target-specific binding partner forms a molecular complex that includes both a target and a probe. A target-specific binding partner has affinity for the target such that it does not substantially bind to other molecules in the sample to the extent that such nonspecific binding interferes with the desired experimental outcome, for example by creating unwanted background signal.

The target-binding functionality and the probe-binding functionality can be contained within one molecule or two or more non-covalently bound molecules. For instance, Example 1 below describes target-specific binding partners that contain an antibody portion that provides target-binding functionality, and a nucleic acid barcode portion that provides probe-binding functionality. A variety of target-specific-binding partners comprising antibody portions and nucleic acid portions are described, for example, in U.S. Pat. No. 9,944,972.

The target-binding functionality of a target-specific binding partner can be imparted, for example, by an antibody, an antibody fragment (e.g., Fab, Fab', F(ab')2, single heavy chain, diabody, and the like), an aptamer, a polypeptide, peptide (e.g., a ligand), a nucleic acid, or small molecule (e.g., a suicide substrate of an enzyme of interest). The target-binding functionality will generally be selected based on the character of the target. For example, when the target is a protein, an antibody can often provide the needed selective target-binding functionality.

Similarly, the probe-binding functionality of a target-specific binding partner will be matched to the probe used. For example, when the probe contains a nucleic acid sequence, a complementary nucleic acid sequence can provide the needed probe-biding functionality. However, probe-binding functionality can be imparted by a variety of partners, including by an antibody, an antibody fragment (e.g., Fab, Fab', F(ab')2, single heavy chain, diabody, and the like), an aptamer, a polypeptide, peptide (e.g., a ligand), a nucleic acid, small molecule (e.g., a suicide substrate of an enzyme of interest), and the like.

A nucleic acid portion of a target-specific binding partner, whether it imparts target-specific binding functionality or probe-specific binding functionality, and a nucleic acid portion of a background-reducing agent, can contain DNA, RNA, a nucleic acid analog (for example, nucleic acid containing an altered phosphate backbone, an altered pentose sugar, and/or altered nucleobases, such as a nucleic acid containing 2'-O-Methyl ribonucleic acid, 2'-fluoro ribonucleic acid, peptide nucleic acid, morpholino and locked nucleic acid, glycol nucleic acid, and threose nucleic acid), or a combination thereof. The nucleic acid portion can be double stranded, single stranded, or a combination thereof.

As generally used herein, the term "nucleic acid" means a polymeric form of nucleotides of any length, such as deoxyribonucleotides or ribonucleotides, or analogs thereof. For example, a nucleic acid may be DNA, RNA or the DNA product of RNA subjected to reverse transcription. Non-limiting examples of nucleic acids include coding or non-coding regions of a gene or gene fragment, loci (locus) defined from linkage analysis, exons, introns, messenger RNA (mRNA), transfer RNA, ribosomal RNA, ribozymes, cDNA, recombinant nucleic acids, branched nucleic acids, plasmids, vectors, isolated DNA of any sequence, isolated RNA of any sequence, nucleic acid probes, and primers. Other examples of nucleic acids include, without limitation, cDNA, aptamers, and peptide nucleic acids ("PNA"). A nucleic acid may comprise modified nucleotides, such as methylated nucleotides and nucleotide analogs ("analogous" forms of purines and pyrimidines are well known in the art). If present, modifications to the nucleotide structure may be imparted before or after assembly of the polymer. A nucleic acid may be a single-stranded, double-stranded, partially single-stranded, or partially double-stranded DNA or RNA, depending on the application.

The term "nucleic acid barcode," as used herein means a single stranded nucleic acid segment, contained within a target-specific binding partner, that binds selectively to its complementary sequence within a cognate probe. The number of nucleotides in a barcode will be sufficient to permit specific complementary binding to the probe under selected reaction conditions. Those skilled in the art can design or empirically determine barcode and matching complementary sequences suitable for use under selected temperatures, salt concentrations, and other reaction conditions. Software resources for designing nucleic acid molecules include, for example, www.nupack.org; Vienna RNA secondary structure server (see, e.g., Vienna RNA secondary structure server Hofacker, Nucleic Acids Research, Volume 31, Issue 13, 1 Jul. 2003, Pages 3429-3431; Abdulkadir Elmas, Guido H. Jajamovich, Xiaodong Wang, and Michael S. Samoilov. Nucleic Acid Therapeutics, Volume: 23 Issue 2: Apr. 4, 2013. Accordingly, a barcode can be, for example, between about 5 to 20 nucleotides long, between about 8 to 15 nucleotides long, and between about 10 to 14 nucleotides long.

Each nucleic acid barcode contains a known sequence, allowing each target-specific binding partner used in a particular assay to be distinctly identified by its barcode. FIG. 2A illustrates nine different target-specific binding partners bound, via barcodes, to complementary regions on probes. Each barcode is distinct, permitting nine distinct probes to be used to identify each target-specific binding partner. Exemplary barcodes and corresponding complementary sequences are shown in Table 1, below.

TABLE 1

| Barcode sequence | SEQ ID NO | Complementary sequence | SEQ ID NO |
|---|---|---|---|
| 5'- ACGGAACCAACA -3' | 1 | 5'- TGTTGGTTCCGT -3' | 13 |
| 5'- ACGGAATGAGGC -3' | 2 | 5'- GCCTCATTCCGT -3' | 14 |
| 5'- ACTTGCTGACGA -3' | 3 | 5'- TCGTCAGCAAGT -3' | 15 |
| 5'- TCACGTCAGCAT -3' | 4 | 5'- ATGCTGACGTGA -3' | 16 |
| 5'- TTGACGATGGCA -3' | 5 | 5'- TGCCATCGTCAA -3' | 17 |
| 5'- GGGAAGTAGGGC -3' | 6 | 5'- GCCCTACTTCCC -3' | 18 |
| 5'- CCCAAAACGTCG -3' | 7 | 5'- CGACGTTTTGGG -3' | 19 |
| 5'- TCGCTGTCATGA -3' | 8 | 5'- TCATGACAGCGA -3' | 20 |
| 5'- AGCAATTCGGGT -3' | 9 | 5'- ACCCGAATTGCT -3' | 21 |
| 5'- CGGGTTAAGGGT -3' | 10 | 5'- ACCCTTAACCCG -3' | 22 |
| 5'- GCGTTGGGATGA -3' | 11 | 5'- TCATCCCAACGC -3' | 23 |
| 5'- AGCGAGGAAAGT -3' | 12 | 5'- ACTTTCCTCGCT -3' | 24 |

A probe useful in the methods described herein can contain one or more nucleic acid barcodes, which can be present on the probe when contacted with a sample, or generated by amplification when contacted with the sample. FIGS. 3A-3C depict a probe-set bound to target-specific binding partners having multiple barcodes. A variety of nucleic acid amplification methods can be used to increase the number of nucleic acid barcodes contained in a target-specific binding partner. Exemplary methods include polymerase chain reaction (PCR) (see, for example, McPherson M J, S G Moller, R Beynon, and C Howe 2000 PCR: Basics from Background to Bench. Heidelberg: Springer-Verlag); rolling circle amplification (RCA) (see, for example, Ali M M et al. Rolling circle amplification: A versatile tool for chemical biology, materials science and medicine. Chemical Society Reviews. 2014; 43(10):3324-3341); primer exchange reaction (PER) (see, for example, WO 2017/143006 A1; Kishi, et al. Nat Chem., 10(2): 155-164); DNA toehold-based strand displacement (see, for example, Schweller et al. PMCID: PMC3517005); hybridization chain reaction (HCR) (see, for example, Dirks et al., 2014, PMID: 15492210, 24712299); DNA hairpin-based dendrimerization reaction (see, for example, Yin et al., 2008, PMID 18202654); and any other method. Multiple types of amplification can even be used in combination. For example, Gusev et al reported combining rolling circle amplification and HRP-based signal amplification (Gusev, Y et al. Am. J. Pathology, vol. 159, 1 (2001): 63-9. doi:10.1016/S0002-9440(10)61674-4). Amplification methods have been described for target-specific binding partners containing DNA barcodes, for example, in US 2018/0164308A1, which is incorporated herein by reference. Therefore, amplified nucleic acid barcodes can be present in a variety of structural forms, including linear and branched forms, and can be within a target-specific binding partner or in one or more molecules bound to a target-specific binding partner, as described in US 2018/0164308A1.

In an embodiment, a nucleic acid barcode is amplified by RCA using a circular DNA template. The template is bound to the nucleic acid sequence of the target-specific binding partner; polymerase is added; and concatemeric repeats of the nucleic acid barcode are created. In an embodiment, a nucleic acid barcode is amplified by PER, which isothermally produces single-stranded DNA with user-prescribed sequences using a strand-displacing polymerase. As described in Kishi, et al. Nat Chem., 10(2): 155-164, the PER process begins by designing a primer. Here, the primer would contain a nucleic acid barcode sequence or portion thereof. Utilizing a catalytic DNA hairpin mediator, PER then appends to the existing primer a new primer with an independent, user-specified sequence. The newly extended primer can then trigger the next step extension, thus forming a programmable PER cascade to autonomously grow a nascent DNA strand along a prescribed pathway to produce a user-prescribed sequence.

A nucleic acid barcode of a target-specific binding partner can be amplified prior to contact with the sample or while in contact with the sample. When amplification is performed in contact with the sample, probes are generally applied after amplification. In some embodiments, the number of barcodes is greater than one; greater than two; greater than five; greater than 10; greater than 20; greater than 50; greater than 100.

Detection of Labels

A variety of detection modalities can be applied to the described methods. A label can be detected, for example, by an optical signal, an electromagnetic signal (across the entire electromagnetic spectrum), an atomic/molecular mass (e.g., detectable by mass spectrometry), tangible mass (e.g., detectable by atomic force microscope), an electrical signal (e.g., current or voltage); a mechanical signal (e.g., acoustic, pressure or other signal) and other methods. Specific detection methods include light spectroscopy, fluorescence spectroscopy, RAMAN spectroscopy, mass spectrometry, ion mobility spectrometry, secondary ion mass spectrometry (SIMS), Auger electron spectroscopy, X-ray photoelectron spectroscopy (XPS), surface plasmon resonance, and myriad other detection methods. The type of detection selected will therefore depend on the label(s) used. The type of sample and assay format will also influence choice of detection mode. The examples below describe use of detection modes including fluorescence microscopy (which can produce images in a direct or reconstructed manner); a fluorescence spectrometer in a plate reader; and a fluorescence spectrometer in a flow cytometry device. Any device or instrument capable of detecting a signal produced by a selected label can be used in a method described herein.

Labels

Given that a variety of detection modalities can be used with the probe-sets described herein, the user can select a variety of labels appropriate for the selected detection modality. As used herein, the term "label" means a detectable moiety that generates a sufficient signal to be registered by a device or instrument configured to read the detectable moiety. The term "label" includes a detectable moiety generated when an enzyme associated with a probe is contacted with a substrate and converts the substrate into a detectable moiety that generates a sufficient signal to be registered by a device or instrument configured to read the detectable moiety. Exemplary labels include chromogenic, optical, fluorescent, chemiluminescent, magnetic, plasmonic, mass-based, electrochemical labels, and phenolic substrates (e.g., tyramine and tyrosine) acted upon by horseradish peroxidase. Accordingly, labels having a variety of chemical structures are useful in the described methods and compositions. As used herein, the term "released label" means the portion of probe containing a label, which has been cleaved by the cleavage agent. As a consequence, the label-containing portion is partially or fully dissociated from its parent molecule or complex.

In some embodiments, a released label contains a nucleotide sequence capable of binding to a background-reducing agent containing a complementary nucleotide sequence.

In an embodiment, a fluorescent label is used. General categories of fluorescent labels include organic dyes, biological fluorophores, quantum dots, and nanoparticles including carbon dots. Specific fluorescent dyes include fluorescein, rhodamine, cyanine dyes, ALEXA dyes, DYLIGHT dyes, and ATTO dyes. The Examples herein describe use of four spectrally distinct fluorescent labels in a single round of detection. It is possible to use more than four spectrally overlapping fluorophores in one round of detection. Use of software to assist in detecting fluorophores having overlapping signals is known (see for example, U.S. Pat. No. 6,750,964). A variety of fluorescent dyes and filters are commercially available, allowing the methods described herein to be performed using any feasible number of fluorescent labels. As described herein, in an embodiment, the methods can be performed using a single fluorescent label; two fluorescent labels; three fluorescent labels; four fluorescent labels; five fluorescent labels; six fluorescent labels; seven fluorescent labels; eight fluorescent labels; and greater than eight fluorescent labels. FIGS. 1A-1D depict a probe-set that can be employed using a single fluorescent label because each round of detection is independent. FIG. 2A depicts three probe-sets where all probes of the first probe-set (A) have the same label; all probes of the second probe-set (B) have the same label; and all probes of the third probe-set (C) have the same label. Thus, in an embodiment, the first and second (and optionally third and/or subsequent) detectable labels are the same. In another embodiment, the first and second (and optionally third and/or subsequent) detectable labels are different.

Generally, when using more than one fluorescent label, signals are detected in different detection channels which correspond to different regions of the light spectrum. Table 2 below shows four detection channels and representative popular fluorophores. If desired, a probe-set can be designed for detection in a particular detection channel. Thus, a collection of probe-sets can be designed for detection in different detection channels such that all first probes are detected in a first detection channel; all second probes are detected in a second detection channel; and, when present, all third probes are detected in a third detection channel. Likewise for subsequent probes. In this embodiment, the labels within a probe-set can be the same, or can be different but detectable in the same detection channel. However, it is not necessary for probe-sets to be aligned with each other in this manner. Because the methods can employ a variety of labels, each round of detection can employ a different detection channel or detection modality if desired. Using different modalities can expand the number of labels available to the user when designing probes as described herein.

TABLE 2

| Microscope Detection Channel | Emission Detection Wavelength Range (nm) | Example Fluorophores |
|---|---|---|
| "FITC" | 510-530 | FITC, FAM, Fluorescein, Cy2, Alexa Fluor 488, Atto 488, |
| "TRITC" | 570-590 | TRITC, TAMRA, Cy3, Quasar 570, Alexa Fluor 568, Atto 550 |

TABLE 2-continued

| Microscope Detection Channel | Emission Detection Wavelength Range (nm) | Example Fluorophores |
|---|---|---|
| "Cy5" | 670-690 | Cy5, Alexa Fluor 647, Atto 647N, Quasar 670 |
| "Cy7" | 750-780 | Cy7, Alexa Fluor 750, Atto 740, IRDye 750 |

Exemplary chromogenic labels include diaminobenzidine (DAB), nitro blue tetrazolium chloride (NBT), 5-bromo-4-chloro-3-indolyl phosphate (BCIP), and 5-bromo-4-chloro-3-indoyl-β-D-galactopyranoside (X-Gal). A label can be a moiety that operates through scattering, either elastic or inelastic scattering, such as nanoparticles and Surface Enhanced Raman Spectroscopy (SERS) reporters (e.g., 4-Mercaptobenzoic acid, 2,7-mercapto-4-methylcoumarin). A label can also be a chemiluminescence/electrochemiluminescence emitter such as ruthenium complexes and luciferases.

Results of Detection

Data outputs from detection of labels using a probe-set described herein can be used to determine the presence, absence, and/or location of target molecules in a sample. The particular data output will depend on the detection method. For example, when a fluorescence microscopy method is used as described in the Examples below, software for aligning fluorescence microscopy images is well known and available from commercial and public sources (e.g. HALO software (Indica Labs), ZEN software (Zeiss), ImageJ: (imagej.nih.gov/ij/download.html).)

The methods described herein involve detecting targets in a "sample." As used herein, the term "sample" means any natural or man-made biological fluid, cell, tissue, or fraction thereof, or other material, that includes or is suspected to include a target. A sample can be derived from a prokaryote or eukaryote and therefore can include cells from, for example, animals, plants, or fungi. Accordingly, a sample includes a specimen obtained from one or more individuals or can be derived from such a specimen.

For example, a sample can be a tissue section obtained by biopsy, or cells that are placed in or adapted to tissue culture. Exemplary samples include biological specimens such a cheek swab, amniotic fluid, skin biopsy, organ biopsy, tumor biopsy, blood, urine, saliva, semen, sputum, cerebral spinal fluid, tears, mucus, and the like. A sample can be further fractionated, if desired, to a fraction containing particular cell types. For example, a blood sample can be fractionated into serum or into fractions containing particular types of blood cells. If desired, a sample can be a combination of samples from an individual such as a combination of a tissue and fluid. A sample can be, or can contain, a laboratory preparation that includes or is suspected to include a target.

When used in a method described herein, an assay component such as a sample, target-specific binding partner, background-reducing agent, or other element, can be attached to a surface. Exemplary surfaces include a slide, a plate, a bead, a tube, and a capillary. Examples 1 and 6-8 describe examples of use of tissue samples attached to slides. Example 2 describes an exemplary use of target-specific binding partners attached to an assay plate. Example 3 describes an exemplary use of target-specific binding partners attached to a bead.

Prior to analysis, a sample can be processed to preserve the integrity of targets. Such methods include the use of appropriate buffers and/or inhibitors, including nuclease, protease and phosphatase inhibitors, that preserve or minimize changes in the molecules in the sample. Methods for preserving tissue samples are well known and include fixatives. The particular preservation method selected will depend on the tissue or cell sample, and the molecular attributes of the target-specific binding partners selected.

As used herein, the term "cleavage site" with reference to a probe described herein means a structure within the probe that is susceptible to the action of its corresponding cleavage agent. Upon contacting a cleavage agent with its corresponding cleavage site, one or more bonds are cleaved. As used herein, to "cleave" a chemical bond encompasses one or more of: breaking, isomerizing, and/or modifying a covalent or noncovalent bond. In some cases, cleavage of a cleavage site therefore results in production of a portion of the probe containing a label ("released label"). In other cases, cleavage may result in a bond modification or isomerization that changes the label character so that it is no longer substantially detected (it is "suppressed"). Thus, the molecular characteristics of a cleavage site depend on its corresponding cleavage agent. A cleavage site can be selected, for example, from a chemical cleavage site; a mechanical cleavage site; an electromagnetic cleavage site; an enzymatic cleavage site.

Therefore, a variety of cleavage agents are useful in the methods and compositions described herein. A cleavage agent can be a chemical agent, enzymatic agent, electromagnetic agent (e.g., UV light, visible light, infrared, near infrared, x-ray, microwave, radio waves, gamma rays), mechanical force (including an acoustic force), or any other agent that suppresses or releases a probe segment, for example, by breaking, isomerizing, and/or chemically modifying a bond. The purpose of label cleavage (leading to release or suppression) is to reduce the signal to a level that does not interfere with detection of subsequent labels, or that is otherwise acceptable to the user. For example, when using fluorescent labels, cleaving bonds of a fluorophore can destroy its fluorescence or alter the wavelength at which its fluorescence is substantially detected.

Exemplary chemical bonds that can be cleaved are disulfide bonds (cleaved by reducing agents such as dithiothreitol or tris(2-carboxyethyl)phosphine)), esters (cleaved by hydroxylamine), vicinal diols (cleaved by sodium metaperiodate), sulfones (cleaved under basic conditions), photocleavable bonds (cleaved by light), and bonds that can be cleaved using enzymes such as proteases, hydrolases, nucleases, uracil DNA glycosylase, and DNA glycosylase-lyase Endonuclease VIII, (e.g., USER (Uracil-Specific Excision Reagent) (New England Biolabs). Non-natural nucleotides, amino acids, or other compounds that serve as substrates for particular enzymes can be used in a cleavage site. For example, 8-oxoguanine may be cleaved by DNA glycosylase OGG1. For example, a 1',2'-Dideoxyribose, dSpacer, apurinic/apyrimidinic, tetrahydrofuran, or abasic furan may be cleaved by Endonuclease VIII cleavage sites.

In an embodiment, an electromagnetic cleavage site is a photocleavage site, which is cleaved by the presence of light of a particular spectral range. A variety of photocleavable moieties can be used in the probes described herein. A variety of chemical bonds are susceptible to photocleavage (see, for example, Olejnik et al., *Nucleic Acids Res.* 1999 Dec. 1; 27(23):4626-31; and Leriche et al. *Bioorganic & Medicinal Chemistry*, volume 20(2), 571-582 (2012).) Among well-known photocleavable moieties include o-nitrobenzyl (ONB) esters, α-thioacetophenone moieties, and 7-amino coumarin moieties. See, for example, CRC Handbook of Organic Photochemistry and Photobiology, 2nd Edition, chapter 69. Exemplary photocleavable moieties that can be incorporated into oligonucleotides are commercially available through Biosynthesis, Inc., Lewisville, Tex.; Integrated DNA Technologies, Coralville, Iowa, and other companies.

A variety of enzymatically cleavable moieties can be used in the probes described herein. A number of enzymes can break the covalent bonds within a nucleic acid molecule. For example, glycosylases can remove a base from the sugar moiety of a nucleotide; endonucleases, exonuclease, DNAzymes, and deoxyribozymes can cleave phosphodiester bonds of nucleic acid molecules, and enzymes can be engineered for cleaving at a cleavage site within a probe described herein.

A glycosylase capable of specifically removing a base that participates in nucleotide base-pairing can reduce the strength of interaction between the two strands. For example, deoxyuridine (dU) can be substituted for deoxythymidine (dT) at a cleavage site; dU would pair with dA, and this pair would be cleaved by Uracil-DNA Glycosylase (UDG, commercially available from New England Biolabs, Cat #M0280S). This reaction will result in abasic site(s) at the cleavage site. Such abasic sites can be further cleaved by Endonuclease VIII, or another method. This promotes dissociation of remnant binding pairs. UDG or a combination of UDG and Endonuclease VIII can therefore be useful in performing the methods described herein. A mixture of these enzymes is commercially available (e.g., from New England Biolabs, under the tradename USER, Cat #M5505S).

A UDG cleavage site useful in the described probes will contain a number of dU nucleotides, ranging from 1 to 5 dUs; 1 to 10 dUs; 1 to 15 dUs; and 1 to 20 dUs. When using UDG and Endonuclease VIII, the dUs can be placed in a way that, after removal of dU, the remnants are short (e.g., less than or equal to about 9, 8, 7, 6, 5, 4, 3, 2, or 1 nucleotides) such that they dissociate spontaneously and relatively quickly. When using UDG (i.e., no Endonuclease VIII) removal of dU units could destabilize the strand enough to separate a label from a quench moiety.

Endonucleases having site specific activity useful in the methods described herein include restriction endonucleases, zinc finger nucleases, transcription activator-like effector nucleases (TALENs), and deoxyribozymes.

An RNA guided endonuclease can be used in methods described herein. For example, Cas9 (CRISPR associated protein 9) is an RNA-guided endonuclease can specifically cleave an engineered cleavage site. One strand may be cleaved, for example using a nicking endonuclease. As an example, Cas9 nickases are Cas9 enzymes that have been engineered to only include one active cleaving site, leading to single strand cuts, while conserving the high specificity of Cas9.

A variety of protein cleavage chemistries can be used in methods described herein, including protein modification chemistries. Some methods modify native amino acids while others require genetic manipulation of the amino acid sequence before modification. Examples include: Yu, Y. et al. Chemoselective peptide modification via photocatalytic tryptophan β-position conjugation. J. Am. Chem. Soc. 140, 6797-6800 (2018); Willwacher, J., Raj, R., Mohammed, S. & Davis, B. G. Selective metal-site-guided arylation of proteins. J. Am. Chem. Soc. 138, 8678-8681 (2016); Krall, N., da Cruz, F. P., Boutureira, O. & Bernardes, G. J. L. Site-selective protein-modification chemistry for basic biology and drug development. Nat. Chem. 8, 103-113 (2016).

In an embodiment, a suitable cleavage agent is capable of breaking covalent bonds within a probe to release a segment (where the segment can contain, for example, a label, quench moiety, or other unwanted segment). Examples of cleavage agents and cleavage modes are shown in FIGS. 4A-4D as described above. One or more combination of different types of cleavage agents and different types of cleavage sites may be used. For example, in a probe-set, one or more probes contain a cleavage site for releasing a label (FIG. 4B); and one or more probes contain a cleavage site for unquenching a label (FIG. 4D). One or more probes can contain both a cleavage site for releasing a label and a cleavage site for unquenching a label. In an embodiment, a cleavage agent is capable of releasing a label (or labels) and unquenching a different label (or labels). If desired, a combination of cleavage agents can be used in any step in which a single cleavage agent is used.

Depending on the nature of the probes and cleavage agent used in a particular step of a method described herein, the methods can involve washing a sample after contacting the sample with a cleavage agent. This step can be useful for removing unwanted signal from released labels; for removing cleavage agent used in a prior step. In an embodiment, washing is not needed. For example, washing is not needed when the signal of the released label does not interfere with the user's experimental intent, such as when the label is suppressed upon treatment by the cleavage agent; or the released label diffuses way or otherwise does not create significant background. Therefore, in certain embodiments, when performing the method on a sample underneath a coverslip or other enclosure, it is not necessary to remove or otherwise disturb the enclosure when carrying out one or more steps of the method. As described below, a background-reducing agent can be employed when carrying out methods without directly accessing a sample, for example, without removing a coverslip.

As used herein, the term "quench moiety" means any physical or chemical characteristic of a probe that functions to quench one or more labels of the probe. The signal produced by a label is quenched when the signal is reduced as compared with the signal in the absence of the quench moiety by at least 10%, for example at least 15%, at least 20%, at least 30%, at least 40%, at least 50%, at least 60%, at least 70%, at least 80%, at least 90%, at least 95%, at least 98%, at least 99%, and completely quenched. The level of signal that renders a label undetectable is method-dependent. Thus, the term "undetectable" means a level of signal that is acceptable to the user for the method employed. For example, an undetectable signal produces a signal-to-background ratio that permits detection of a desired signal without interference.

When the label is a fluorophore, the quench moiety reduces the emission from the fluorophore when attached to or in proximity to the fluorophore. Any of a variety of fluorophore quench moieties can be used in a method described herein. Exemplary quench moieties include, but are not limited to, Dabacyl, Cy50, Iowa Black, OXL570, BHQ-I, BHQ-2, BHQ-3, and Si-rhodamine based quenchers. Label-Quencher pairs are well known. Exemplary fluorophores and spectrally compatible quenchers include Coumarin and Dabacyl; ALEXA Fluor 488 and BHQ-1; Cy3 and Iowa Black RQ; TAMRA and OXL570; and IRDye 680 and BHQ-3.

The location of a quench moiety relative to a label will depend on the particular physical and chemical characteristics of the components selected. For a nucleic acid probe, a quench moiety can be attached, for example, on the end of a nucleotide of a probe, internally, on a branched nucleotide segment, or other location so long as the quench moiety is in sufficient proximity to the label. For example, a quench moiety can be attached at the phosphate moiety of the 3' nucleotide of a probe.

A probe can contain a tertiary structure that maintains a label and quencher in close proximity to achieve quenching. Upon treatment with a cleavage agent, such a probe would undergo a conformation change that separates the label and quench moiety to de-quench the label. For example, a nucleic acid hairpin can be destabilized by treatment with uracil-DNA glycosylase, increasing the distance between fluorophore and quench moiety, thereby de-quenching the signal from the fluorophore. For a polypeptide probe, a variety of tertiary structures can be engineered into a polypeptide to achieve a desired distance between a label and quench moiety (see, for example, Chen et al., *Can. J. Chem.* 93: 389-398 (2015)).

FIG. 2A illustrates three exemplary probe-sets in which all second probes (B) contain the same quench moiety; and all third probes (C) contain the same quench moiety. This represents the concept that labels are paired with quench moieties that function effectively to render the label undetectable.

The probes and target-specific binding partners described herein can be prepared using standard molecular biology and chemical methods for designing molecules containing two functional sites or joining two or more molecules together to acquire the required functionality. A method for preparing target-specific binding partners that are antibodies with covalently attached nucleic acid strands is described in Wang et al. *Nano Lett.*, 17, 6131-6139 (2017). The procedure involves crosslinking of thiol-modified DNA oligonucleotides to lysine residues on antibodies, as described in Agasti et al, *Chem Sci,* 8, 4, 3080-3091 (2017). In brief, 250 uM 5' thiol-modified DNA oligonucleotides (Integrated DNA Technologies) were activated by 100 mM DTT for 2 hours and then purified using NAP5 columns (GE Healthcare Life Sciences, 17-0853-02) to remove excessive DTT. Antibodies formulated in PBS were concentrated using 100 KDa Amicon Ultra Filters (EMDMillipore, UFC510096) to 2 mg/ml and reacted with maleimide-PEG2-succinimidyl ester crosslinkers (Sigma 746223) for 2 hours. Antibodies were then purified using 0.5 ml 7 kDA Zeba desalting columns (LifeTechnologies, 89883) to remove excessive crosslinkers. Activated DNA oligonucleotides were incubated with antibodies (11:1 DNA: Antibody ratio) overnight at 4° C. Final conjugated antibodies were washed using PBS/BSA (100 ug/ml) using Amicon Ultra Filters four times to remove nonreacted DNA oligonucleotides. An alternative method is to employ the SiteClick kit from ThermoFisher (S10467).

The skilled artisan will understand that the figures, described above, and example, described below, are for illustration purposes only. Neither the figures nor the examples are intended to limit the scope of the disclosed teachings in any way.

EXAMPLES

The following examples are provided to illustrate certain disclosed embodiments and are not to be construed as limiting the scope of this disclosure in any way.

Example 1

This example shows detection of eight distinct targets on a single formalin-fixed paraffin-embedded (FFPE) tonsil slide using a Tris(2-carboxyethyl)phosphine (TCEP) based cleavage mode.

A human tonsil tissue slide (Amsbio LLC, Cambridge, Mass.) was first baked for 30 min at 60° C. and then deparaffinized in a GEMINI automated slide stainer (ThermoFisher). The slide was then washed three times in PBS, before blocking with the Ultivue antibody diluent solution (UltiMapper™ I/O kits, Ultivue, Cambridge, Mass.) for 15 min at room temperature. Eight different antibodies (selective for CD45RO, PD1, CD3, Cytokeratin, CD8, CD68, PD-L1 and Ki67) conjugated with distinct DNA barcodes were together added to the tissue slide and incubated for 1 hr. at room temperature (see Table 1 for exemplary nucleic acid bar codes). The slide was then washed three times in PBS, followed by incubation with Ultivue pre-amplification mix (UltiMapper™ I/O kits) for 25 min. at room temperature. The slide was then washed three times in PBS; Ultivue amplification solution (UltiMapper™ I/O kits) was the added to the slide and incubated for 90 min. at 30° C. in a hybridization oven (SLIDE MOAT, Boekel, Feasterville, Pa.). The slide was then washed three times in PBS followed by incubation with Ultivue nuclear counterstain (UltiMapper™ I/O kits) for 15 min. at room temperature in a dark environment. The slide was then washed three times in PBS. A cocktail containing all eight fluorescent probes (probe-set design as shown in FIGS. 1A-1B) diluted in Ultivue probe buffer (UltiMapper™ I/O kits) was added to the slide and incubated for 25 min. at room temperature in a dark environment. The slide was then washed three times in PBS, mounted in PBS and coverslipped.

The whole tissue fluorescence image for round 1 was then acquired on a PerkinElmer Polaris microscope at 20× magnification. Following the acquisition of the round 1 image, the slide was de-coverslipped and incubated with about 10 molar equivalents TCEP for 15 minutes at room temperature. The slide was washed three times in PBS, mounted in PBS and coverslipped. The whole tissue fluorescence image for round 2 was then acquired at 20× magnification.

FIGS. 6A-6B show results demonstrating detection of eight unique protein targets on a single FFPE tonsil slide using TCEP based cleavage mode in two detection rounds (FIGS. 6A and 6B; four targets for each round) without the addition of probes between the detection rounds. Probes for CD45RO, PD1, CD3 and Cytokeratin, have a disulfide cleavage site between the barcode recognizing domain and the respective fluorescent dyes. Probes for CD8, CD68, PDL1 and Ki67 have a disulfide cleavage site between the respective fluorescent dyes and the quench moieties (see, for example, FIG. 4B for a schematic).

The fluorescent dyes were selected to be detected in four different detection channels: FITC, TRITC, Cy5 and Cy7 (see Table 2). Specific signal was observed for CD45RO, PD1, CD3 and Cytokeratin targets in round 1 of detection (FIG. 6A). No detectable signal is observed for CD8, CD68, PDL1 and Ki67 targets in round 1 of detection (FIG. 6A) as the fluorescence signal is initially suppressed by the quench moiety. Post-TCEP treatment, which facilitates simultaneous release of the fluorescent dye and de-quenching of the specific signal, the specific signal is observed for CD8, CD68, PDL1 and Ki67 targets in round 2 of detection (FIG. 6B). No detectable signal is observed for CD45RO, PD1, CD3 and Cytokeratin targets in round 2 of detection.

Thus, a probe-set as described herein was useful for detecting eight targets in two rounds of detection.

Example 2

This example describes detection of eight unique targets in a plate-based assay using a TCEP based cleavage mode.

Nunc MaxiSorp (Thermo Fisher) microplate wells are coated with a mixture of capture antibodies (Abcam) to Human IFN alpha, IL-6, TNF alpha, IFN gamma, IFN beta, IFN lambda, IL-1a, and IL-4 at a total antibody concentration of 5 µg/ml in 10 mM phosphate buffered saline, pH 7.2 (PBS) for 2 hr at ambient temperature. The wells are aspirated and blocked with PBS containing 2% bovine serum albumin overnight at ambient temperature. The wells are aspirated and samples and standards are added for 2 hr at 37° C. The wells are washed with PBS containing 0.05% Tween-20 (PBST). A mixture of eight target-specific binding partners, which are antibodies to Human IFN alpha, IL-6, TNF alpha, IFN gamma, IFN beta, IFN lambda, IL-1a, and IL-4 conjugated with unique DNA barcodes (see Table 1 for exemplary nucleic acid bar codes), is added to each well for 1 hr. at ambient temperature. The wells are washed with PBST, followed by incubation with Ultivue pre-amplification mix (UltiMapper™ I/O kits) for 25 min. at ambient temperature. The wells are washed with PBST and the DNA barcodes are amplified as described in WO2018/107054, which is incorporated herein by reference. The wells are washed with PBST and a cocktail containing all eight fluorescent probes complimentary to the DNA barcodes (Human IFN alpha, IL-6, TNF alpha, IFN gamma as the first probe (A) in FIG. 1A; IFN beta, IFN lambda, IL-1a, and IL-4 as a probe similar to the second probe (B) in FIG. 1B but without the second cleavage site ($C_2$)) diluted in Ultivue probe buffer (UltiMapper™ I/O kits) is added and incubated for 25 min. at ambient temperature in a dark environment. The wells are washed with PBST, and first round of fluorescence detection (Human IFN alpha, IL-6, TNF alpha, IFN gamma) is performed on a Synergy H1 Microplate Reader (BioTek).

Following fluorescence detection of the first round signals, TCEP is added and incubated for 15 min. at ambient temperature, which removes the first round signals and exposes the second round signals. The wells are washed with PBST and the second round of fluorescence detection (IFN beta, IFN lambda, IL-1a, and IL-4) is performed.

Controls containing standard concentrations of analytes are employed, to that concentrations of target molecule can be determined if desired. The results provide an 8-plex analysis of the presence or absence, or concentrations of, the targets in each sample.

Example 3

This example describes detection of eight unique targets in a bead-based immunoassay using a TCEP based cleavage mode.

Capture antibodies for each target are immobilized on Dynabeads, M-270 epoxy, 2.8 µm in diameter (ThermoFisher) according to the manufacturer's instructions. The beads are blocked and incubated with target-specific binding partners and a probe-set essentially as described in Example 2. Fluorescence detection of first round signals is performed on a flow cytometer, followed by TCEP incubation and detection of second round signals.

Example 4

This example describes detection of a target using a probe with a uracil DNA glycosylase cleavage agent.

Figure 7A:
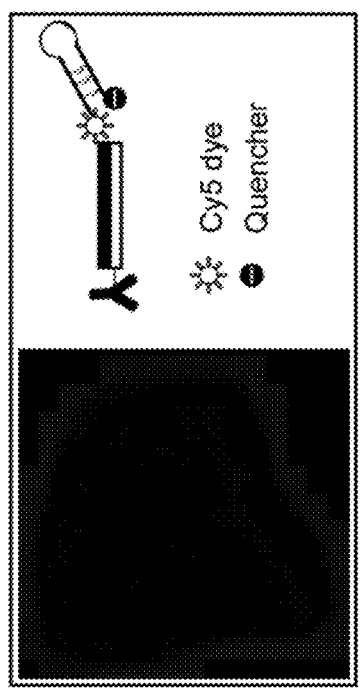
FIGS. 7A-B show images of a first round of detection in which the probe is quenched (7A) and second round of detection in which the probe is unquenched upon treatment with a cleavage agent (7B), in a tissue sample using an embodiment of the present disclosure.
Figure 7B:
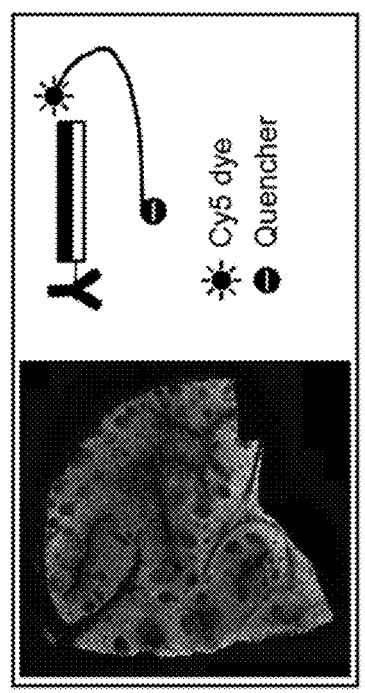

This example shows use of a probe as depicted in FIGS. 7A-7B, right panel. A sample was prepared essentially as described in Example 1, but for a single target, CD3. The sample was incubated with target-specific binding partner for CD3 and a probe containing a unique nucleic acid barcode; a fluorescent label, and a corresponding quench moiety (FIGS. 7A-7B, right panel).

The sample was imaged to detect the fluorescent label. FIG. 7A shows that no signal was detected, demonstrating that the label was quenched. The sample was then treated with uracil DNA glycosylase (New England Biolabs; 0.1 Units/ul Uracil DNA Glycosylase in 1× Cut Smart Buffer incubated on the tissue sample at 37C for 15 mins. (see www.neb.com/products/b7204-cutsmart-buffer#Product%20Information) and re-imaged. FIG. 7B shows that the label was unquenched, thereby activating signal from the label.

Example 5

This example describes detection of three miRNA targets using a TCEP based cleavage mode.

Target-specific binding partners for miRNA targets contain DNA sequences that recognize the particular miRNAs. For example, a DNA sequence selective for miR-146a is 5'-AACCCATGGAATTCAGTTCTCA-3' (SEQ ID NO: 25); a DNA selective for miR-15a is 5'-CACAAACCAT-TATGTGCTGCTA-3' (SEQ ID NO: 26); and a DNA sequence selective for MiR-155 is 5' CCCCTATCACGATT-AGCATTAA-3' (SEQ ID NO: 27). These sequences are incorporated into a target-specific binding partner that contains a unique barcode (see, for example, Table 1) for each target. Corresponding probes can be designed to contain sequences complementary to the barcodes (Table 1), and label, quencher, and cleavage site compositions that function to permit sequential detection (see e.g., FIGS. 1A-1D).

The paraffin section is baked at 65° C. for 1 hr, and deparaffinize in xylene (2×10 minutes), rehydrated in ethanol solutions (100%, 90%, 80%, 70%), and DEPC-treated water and PBS wash. The section is incubated with Proteinase K (20 ug/mL) at 37° C. for 10 min., washed with PBS and fixed with 4% paraformaldehyde for 10 min. It is then washed with PBS, 100 mM glycine, PBS, and 2×SSC (diluted from 20×, ThermoFisher). The section is then pre-hybridized in a solution of 50% deionized formamide, 2×SSC, 1×Denhardt's, 0.02% SDS, yeast tRNA (0.5 mg/mL), and salmon sperm DNA (0.5 mg/mL) for 2 hr at 50° C.

The probes are prepared with DNA barcodes on the 3' ends. These are hybridized overnight at 50° C. in a solution of 50% deionized formamide, 2×SSC, 1×Denhardt's, 10% dextran sulfate, yeast tRNA (0.5 mg/mL), and salmon sperm DNA. The section is washed with 2×SSC at 37° C., 2×SCC at 50° C., 1×SSC at 37° C. 1×SCC at 50° C., 0.02% SDS in 1×SSC at 37° C., 1×SSC at 50° C., and PBST at ambient temperature. The section is washed with PBST, followed by incubation with Ultivue pre-amplification mix for 25 min. at ambient temperature. The section is washed with PBST and Ultivue amplification solution is added and incubated for 90 min. at 30° C.

A cocktail containing all fluorescent probes (some prepared as in the first probe (A) in FIG. 1A and others prepared as the second probe (B) in FIG. 1B but without the second cleavage site ($C_2$)), complimentary to the DNA barcodes, is added and incubated for 25 min. at ambient temperature in a dark environment. The first round of fluorescence detection; TCEP incubation; and second round of fluorescence detection are performed essentially as described in Example 1.

Example 6

This example describes detection of eight unique targets on a single formalin-fixed paraffin-embedded (FFPE) tonsil slide using a photocleavage method without coverslip removal.

A human tonsil tissue slide (Amsbio LLC, Cambridge, Mass.) was first baked for 30 min at 60° C. and then processed on a Leica BONDRx autostainer. The slide was deparaffinized using the dewax solution (AR9222, Leica Biosystems) with 4-step dewax protocol and antigen retrieved by incubating epitope retrieval solution 2 (AR9640, Leica Biosystems) for 20 minutes at 100° C. The slide was then washed three times with the Leica wash solution (AR9590, Leica Biosystems), before blocking with the Ultivue antibody diluent solution (UltiMapper™ I/O kits, Ultivue, Cambridge, Mass.) for 15 min at room temperature.

Eight different antibodies (CD8, PD1, PDL1, CD68, CD3, CD4, FoxP3 and Cytokeratin) conjugated with unique DNA barcodes were together added to the tissue slide and incubated for 1 hr at room temperature. The slide was then washed three times with Leica wash solution, followed by incubation with Ultivue pre-amplification mix (UltiMapper™ I/O kits) for 25 min at room temperature. The slide was then washed two times with Leica wash solution followed by incubating the slide with Leica wash solution for 5 min at 35° C. Ultivue amplification solution (UltiMapper™ I/O kits) was then added to the slide and incubated for 90 min at room temperature. The slide was then washed three times with Leica wash solution followed by incubation with Ultivue nuclear counterstain (UltiMapper™ I/O kits) for 15 min at room temperature. The slide was then washed three times with Leica wash solution.

Two probe-sets of four probes each were used. A cocktail containing all eight fluorescent probes (0.5 to 2 µM) diluted in Ultivue probe buffer (UltiMapper™ I/O kits) was added to the slide and incubated for 25 min at room temperature. Probes for CD8, PD1, PDL1 and CD68 (Probe design A in FIG. 11A), contain a UV cleavage site between their barcode complementary regions and the respective fluorescent dyes. The portion of the probe released upon cleavage contains a region complementary to a background-reducing agent present in the mounting medium applied to the sample prior to imaging. Probes for CD3, CD4, FoxP3 and Cytokeratin, (Probe design B in FIG. 11A), contain a UV-activated cleavage site between the respective fluorescent dye and the quencher. The slide was then washed three times in Leica wash solution, mounted in mounting media containing activatable background-reducing agents (100-800 nM) corresponding to each first probe (see FIG. 11A for background-reducing agent design, indicating that the background-reducing agent contained two cleavage sites) and coverslipped with UV clear coverslips.

The fluorescence image for round 1 was then acquired on a Zeiss AxioScan Z1 microscope at 20× magnification. Following the acquisition of the round 1 image, the entire tissue was then scanned using the Colibri7 385 nm LED with a 10× objective with 5 secs exposure to photocleave the cleavage sites on the first probes and corresponding background-reducing agents. The fluorescence image for round 2 was then acquired at 20× magnification immediately.

Figure 11A:
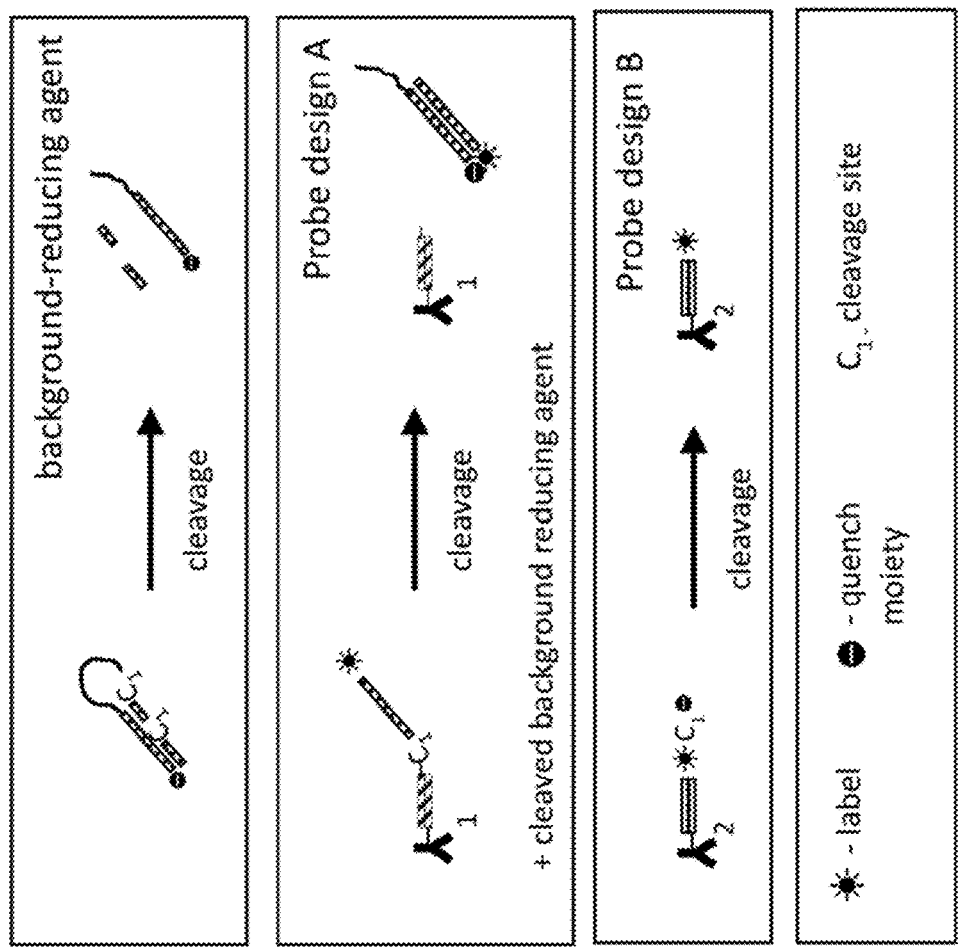

FIGS. 11B-11C show fluorescence signals from the eight unique protein targets. Specific signal observed for CD8, PD1, PDL1 and CD68 targets in round 1 of detection (FIG. 11B). No detectable signal observed for CD3, CD4, FoxP3 and Cytokeratin targets in round 1 of detection (FIG. 11C) as the fluorescence signal is initially suppressed by the quench moiety. Use of UV light as a cleavage agent facilitates simultaneous release of the fluorescent dye for Probe design A (FIG. 11A) and de-quenching of Probe design B (FIG. 11A). Specific signal was observed for CD3, CD4, FoxP3 and Cytokeratin targets in round 2 of detection (FIG. 11C). No detectable specific signal observed for CD8, PD1, PDL1 and CD68 targets in round 2 of detection. Additionally, no detectable fluorescent signal observed in round 2 of detection from the released fluorescent dyes.

Example 7

This example shows the use of background-reducing agents to reduce fluorescence signal from probe labels released from round A probes after photocleavage and without coverslip removal.

Two human tonsil tissue slides (Amsbio LLC, Cambridge, Mass.) were first baked for 30 min at 60° C. and then processed on a Leica BondRx autostainer. The slides were deparaffinized using the dewax solution (AR9222, Leica Biosystems) with 4-step dewax protocol and antigen retrieved by incubating epitope retrieval solution 2 (AR9640, Leica Biosystems) for 20 minutes at 100° C. The slides were then washed three times with the Leica wash solution (AR9590, Leica Biosystems), before blocking with the Ultivue antibody diluent solution (UltiMapper™ I/O kits, Ultivue, Cambridge, Mass.) for 15 min at room temperature. CD3 antibody conjugated with DNA barcodes was added to the tissue slides and incubated for 1 hr at room temperature. The slides were then washed three times with Leica wash solution, followed by incubation with Ultivue pre-amplification mix (UltiMapper™ I/O kits) for 25 min at room temperature. The slides were then washed two times with Leica wash solution followed by incubating the slide with Leica wash solution for 5 min at 35° C. Ultivue amplification solution (UltiMapper™ I/O kits) was then added to the slides and incubated for 90 min at room temperature. The slides were then washed three times with Leica wash solution followed by incubation with Ultivue nuclear counterstain (UltiMapper™ I/O kits) for 15 min at room temperature. The slides were then washed three times with Leica wash solution. Fluorescent probe (probe design as shown in FIGS. 12A, 12C) diluted in Ultivue probe buffer (UltiMapper™ I/O kits) was added to the slides and incubated for 25 min at room temperature. The slides were then washed three times in Leica wash solution. One of the tissue slides was then mounted in the 1×TAE Mg2+ buffer, whereas the other slide was mounted in mounting media containing background-reducing agent in 1×TAE Mg2+ buffer. Both tissues slides were coverslipped with UV clear coverslips.

The whole tissue fluorescence image for round 1 was then acquired on a Zeiss AxioScan Z1 microscope at 20× magnification. Following the acquisition of the round 1 image, the entire tissue was then scanned using the Colibri7 385 nm LED with a 10× objective with 5 secs exposure to photocleave the cleavage sites on the first probes. The whole tissue fluorescence images were then acquired at 20× magnification immediately after photocleavage.

Specific signal was observed for CD3 for both slides (FIGS. 12A and 12C) before photocleavage. No detectable initial quenching was observed for the slide mounted in the presence of photoactivatable background-reducing agent when comparing the signal between the two slides before cleavage. Residual diffused fluorescent signal was observed for the slide (FIG. 12B) in the absence of background-reducing agent in mounting media (see FIG. 12C for background-reducing agent design) after cleavage without coverslip removal. Minimal to no detectable residual fluorescent signal was observed for the slide with background-reducing agent in mounting media (see FIG. 12D) after cleavage without coverslip removal.

Example 8

This example describes detection of sixteen unique targets on a single formalin-fixed paraffin-embedded (FFPE) tonsil slide using three probe-sets and three different cleavage agents.

A human tonsil tissue slide (Amsbio LLC, Cambridge, Mass.) was first baked for 30 min at 60° C. and then processed on a Leica BONDRx autostainer. The slide was deparaffinized using the dewax solution (AR9222, Leica Biosystems) with 4-step dewax protocol and antigen retrieved by incubating epitope retrieval solution 2 (AR9640, Leica Biosystems) for 20 minutes at 100° C. The slide was then washed three times with the Leica wash solution (AR9590, Leica Biosystems), before blocking with the Ultivue antibody diluent solution (UltiMapper™ I/O kits, Ultivue, Cambridge, Mass.) for 15 min at room temperature.

Sixteen different antibodies (CD8, CD68, PDL1, Ki67, CD45RO, PD1, CD3, Cytokeratin, CD11c, GranzymeB, FoxP3, Lag3, CD20, CD163, CD4 and MHCII) conjugated with unique DNA barcodes were together added to the tissue slide and incubated for 1 hr at room temperature. The slide was then washed three times with Leica wash solution, followed by incubation with Ultivue pre-amplification mix (UltiMapper™ I/O kits) for 25 min at room temperature. The slide was then washed two times with Leica wash solution followed by incubating the slide with Leica wash solution for 5 min at 35° C. Ultivue amplification solution (UltiMapper™ I/O kits) was then added to the slide and incubated for 90 min at room temperature. The slide was then washed three times with Leica wash solution followed by incubation with Ultivue nuclear counterstain (UltiMapper™ I/O kits) for 15 min at room temperature. The slide was then washed three times with Leica wash solution. A cocktail containing all 16 fluorescent probes diluted in Ultivue probe buffer (UltiMapper™ I/O kits) was added to the slide and incubated for 25 min at room temperature.

Probes for CD8, CD68, PDL1 and Ki67 have a di-sulfide cleavage site between the probe binding domain and the respective fluorescent dyes (FIG. 13A, probe design 1). Probes for CD45RO, PD1, CD3 and Cytokeratin have a UV-cleavage site between the probe binding domain and the respective fluorescent dyes, and a di-sulfide cleavage site between fluorescent dye and corresponding quenchers (FIG. 13A, probe design 2).

Probes for CD11c, Granzyme B, FoxP3 and LAG3 have uracil bases in the probe binding domain, and a UV-cleavage site between fluorescent dye and corresponding quenchers (FIG. 13A, probe design 3). Probes for CD20, CD163, CD4 and MHCII have a hairpin structure consisting of uridine-adenine base pairs between fluorescent dye and corresponding quenchers (FIG. 13A, probe design 4).

The slide was then washed three times in PBS, mounted in Prolong Gold Antifade Mountant (P36930, Thermo Fisher) and coverslipped. The fluorescence image for round 1 was then acquired on a Zeiss AxioScan Z1 microscope at 20× magnification. Following the acquisition of the round 1 image, the slide was then de-coverslipped and incubated with TCEP for 15 minutes. The slide was then washed three times in PBS, mounted in Prolong Gold Antifade Mountant and coverslipped with UV clear coverslips. The fluorescence image for round 2 was then acquired on a Zeiss AxioScan Z1 microscope at 20× magnification. Following the acquisition of the round 2 image, the entire tissue was then scanned using the Colibri7 385 nm LED with a 10× objective with 5 secs exposure to affect photocleavage. The slide was then de-coverslipped and washed three times in PBS, mounted in Prolong Gold Antifade Mountant and coverslipped. The whole tissue fluorescence image for round 3 was then acquired on a Zeiss AxioScan Z1 microscope at 20× magnification. Following the acquisition of the round 3 image, the slide was then de-coverslipped and incubated with UDG enzyme for 10 minutes at 37° C. The slide was then washed three times in PBS, mounted in Prolong Gold Antifade Mountant and coverslipped. The fluorescence image for round 4 was then acquired on a Zeiss AxioScan Z1 microscope at 20× magnification.

Figure 13B:
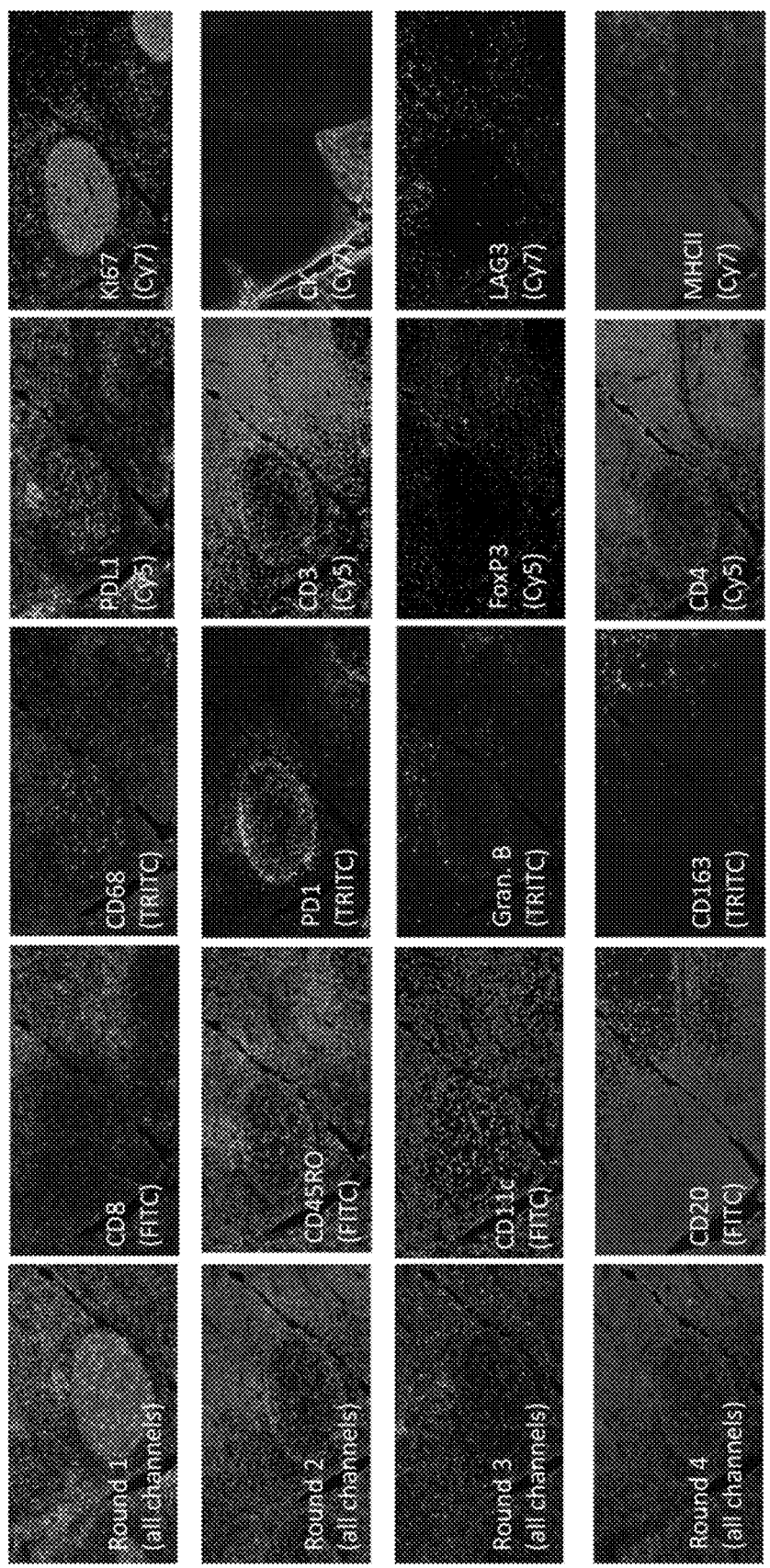

FIG. 13B shows detection of sixteen distinct protein targets on a single FFPE tonsil slide using three different cleavage methods (TCEP, UV and UDG enzyme) in four detection rounds without the addition of probes between the detection rounds. Specific signal observed for CD8, CD68, PDL1 and Ki67 (FIG. 13A, probe design 1) targets in round 1 of detection (FIG. 13B, Round 1) and no detectable signal observed from other targets with other probe designs. Specific signal observed for CD45RO, PD1, CD3 and Cytokeratin (FIG. 13A, probe design 2) targets in round 2 of detection (FIG. 13B, Round 2) after TCEP chemistry and no detectable signal observed from other targets with other probe designs. Specific signal observed for CD11c, Granzyme B, FoxP3 and LAG3 (FIG. 13A, probe design 3) targets in round 3 of detection (FIG. 13B, Round 3) after UV photocleavage and no detectable signal observed from other targets with other probe designs. Specific signal observed for CD20, CD163, CD4 and MHCII (FIG. 13A, probe design 4) targets in round 4 of detection (FIG. 13B, Round 4) after UDG enzyme treatment and no detectable signal observed from other targets with other probe designs.

Example 9. Additional Embodiments

The following numbered items provide additional support for and descriptions of the embodiments herein.

Item 1. A method for detecting a plurality of target molecules, the method comprising:
(a) contacting a sample with two or more target-specific binding partners, wherein each target-specific binding partner comprises a nucleic acid barcode; and is specific for a different target molecule;
(b) contacting the sample with one or more probe-sets wherein each probe in a probe-set is specific for a different target-specific binding partner, and wherein each probe-set comprises:
a first probe, comprising:
  a nucleic acid sequence complementary to a nucleic acid barcode of a corresponding target-specific binding partner;
  a first label; and
  a cleavage site for a first cleavage agent, wherein the first cleavage agent is capable of releasing the first label, and
a second probe comprising:
  a nucleic acid sequence complementary to a nucleic acid barcode of a corresponding target-specific binding partner;

a second label;
  a quench moiety, wherein the quench moiety renders the second label undetectable; and
  a cleavage site for the first cleavage agent, wherein the first cleavage agent is capable of releasing the quench moiety, whereby the second label is rendered detectable; and optionally comprises a cleavage site for a second cleavage agent wherein the second cleavage agent is capable of releasing the second label;
(c) detecting signals corresponding to labels of the first probes of each of the one or more probe-sets;
(d) contacting the sample with a first cleavage agent, thereby releasing the labels of the first probes in each of the one or more probe-sets; and
releasing the quench moieties of the second probes in each of the one or more probe-sets, thereby activating signals corresponding to the second labels, and
(e) detecting signals corresponding to the labels of the second probes of each of the one or more probe-sets.

Item 2. The method of Item 1, wherein one or more of the probe-sets further comprises a third probe, and the method further comprises:
(f) in step (b), contacting the sample with the third probe comprising:
  a nucleic acid sequence complementary to a nucleic acid barcode of a corresponding target-specific binding partner;
  a third label; and
  a quench moiety, wherein the quench moiety renders the third label undetectable; and
  a cleavage site for the second cleavage agent, wherein the second cleavage agent is capable of releasing the quench moiety, whereby the third label is rendered detectable;
  and optionally comprises a distinct cleavage site for a distinct cleavage agent capable of releasing the third label; and
(g) after step (e), contacting the sample with a second cleavage agent, thereby releasing the labels of the second probes in each of the one or more probe-sets; and releasing the quench moieties of the third probes in one or more probe-sets, thereby activating signals corresponding to the third labels; and
(h) detecting signals corresponding to the labels of the third probes of one or more probe sets.

Item 3. The method of Item 2, wherein one or more of the probe-sets further comprise a subsequent probe, and the method further comprises:
(i) in step (b), contacting the sample with a subsequent probe contained in one or more probe-set, wherein the subsequent probe comprises:
  a nucleic acid sequence complementary to a nucleic acid barcode of a corresponding target-specific binding partner;
  a subsequent label; and
  a quench moiety, wherein the quench moiety renders the subsequent label undetectable; and
  a cleavage site for a subsequent cleavage agent, wherein the subsequent cleavage agent is capable of releasing the quench moiety, whereby the subsequent label is rendered detectable;
  and optionally comprises a distinct cleavage site for a distinct cleavage agent capable of releasing activated labels from probes in the sample;
(j) contacting the sample with a subsequent cleavage agent, thereby releasing activated labels of the probes in each probe-set; and releasing the quench moieties of the subsequent probes in each probe-set, thereby activating signals corresponding to the labels of the subsequent probes in each probe-set; and
(k) detecting signals corresponding to the labels of the subsequent probes of each probe-set; and
(l) optionally repeating steps (i) through (k).

Item 4. The method of any one of Items 1-3, wherein the first and second detectable labels of a probe-set are the same.

Item 5. The method of any one of Items 1-3, wherein the first and second detectable labels of a probe-set are different.

Item 6. The method of any one of Items 2-5, wherein the two or more of the first, second, and third detectable labels of a probe-set are the same.

Item 7. The method of any one of Items 2-5, wherein the two or more of the first, second, and third detectable labels of a probe-set are different.

Item 8. The method of any one of Items 3-7, wherein two or more of the first, second, third, and subsequent labels are the same.

Item 9. The method of any one of Items 3-7, wherein two or more of the first, second, third, and subsequent labels are different.

Item 10. The method of any one of Items 1-9, further comprising washing the sample after contacting the sample with the first cleavage agent and/or after contacting the sample with the second cleavage agent.

Item 11. The method of any one of Items 1-9, wherein the sample is not washed after contacting the sample with the first cleavage agent and/or after contacting the sample with the second cleavage agent.

Item 12. The method of Item 11, wherein the coverslip is not removed.

Item 13. The method of any one of Items 1-12, further comprising increasing the number of nucleic acid barcodes on a target-specific binding partner, wherein multiple copies of a corresponding probe bind to multiple copies of the nucleic acid barcode.

Item 14. The method of Item 13, wherein the number of nucleic acid bar codes is increased using rolling circle amplification, primer exchange reaction, hybridization chain reaction, or DNA branching.

Item 15. The method of Item 14, wherein the number of nucleic acid bar codes is increased before the target-specific binding partner is contacted with the sample.

Item 16. The method of Item 14, wherein the number of nucleic acid bar codes is increased when the target-specific binding partner is bound to its target molecule.

Item 17. The method of any one of Items 1-16, wherein the released label of a first probe comprises a nucleotide sequence.

Item 18. The method of Item 17, further comprising contacting the sample with a background-reducing agent comprising a nucleotide sequence complementary to that of the released label of the released first probe, wherein binding of the background-reducing agent to the released label of the released first probe quenches the signal of the label.

Item 19. The method of any one of Items 2-18, wherein the released label of a second probe comprises a nucleotide sequence.

Item 20. The method of Item 19, further comprising contacting the sample with a background-reducing agent comprising a nucleotide sequence complementary to that of the released label of the second probe, wherein binding of the background-reducing agent to the label of the released second probe quenches the signal of the label.

Item 21. The method of any one of Items 3-20, wherein an activated label of a released probe comprises a nucleotide sequence.

Item 22. The method of any one of Items 1-21, further comprising contacting the sample with a background-reducing agent comprising a nucleotide sequence complementary to that of the released label of the probe, wherein binding of the background-reducing agent to the released label of the released probe quenches the signal of the label.

Item 23. A probe-set composition comprising:
one or more first probes, each comprising:
  a nucleic acid sequence complementary to a nucleic acid barcode of a corresponding target-specific binding partner;
  a first label; and
  a cleavage site for a first cleavage agent, wherein the first cleavage agent is capable of releasing the first label, and
one or more second probes, each comprising:
  a nucleic acid sequence complementary to a nucleic acid barcode of a corresponding target-specific binding partner;
  a second label;
  a quench moiety, wherein the quench moiety renders the second label undetectable; and
  a cleavage site for the first cleavage agent, wherein the first cleavage agent is capable of releasing the quench moiety, whereby the second label is rendered detectable;
  and optionally comprises a distinct cleavage site for a distinct cleavage agent capable of releasing the second label.

Item 24. The composition of Item 23, further comprising:
one or more third probes, each comprising:
  a nucleic acid sequence complementary to a nucleic acid barcode of a corresponding target-specific binding partner;
  a third label;
  a quench moiety, wherein the quench moiety renders the third label undetectable; and
  a cleavage site for a second cleavage agent, wherein the second cleavage agent is capable of releasing the quench moiety, whereby the third label is rendered detectable;
  and optionally comprises a distinct cleavage site for a distinct cleavage agent capable of releasing the third label,
wherein the second probe further comprises a cleavage site for the second cleavage agent.

Item 25. The composition of Item 24, further comprising:
a subsequent probe comprising:
  a nucleic acid sequence complementary to a nucleic acid barcode of a corresponding target-specific binding partner;
  a subsequent label;
  a quench moiety for the subsequent label, wherein the quench moiety renders the subsequent label undetectable; and
  a cleavage site, wherein a cleavage agent is capable of releasing the quench moiety, whereby the subsequent label is rendered detectable;
  and optionally comprises a distinct cleavage site wherein a distinct cleavage agent is capable of releasing the subsequent label,
wherein another probe in the probe-set comprises a cleavage site for the same cleavage agent that releases the quench moiety of the subsequent probe.

Item 26. The composition of any one of Items 23-25, wherein the one or more first probes have the same label.

Item 27. The composition of any one of Items 23-25, wherein the one or more first probes have a different label.

Item 28. The composition of any one of Items 23-27, wherein the cleavage site is an electromagnetic cleavage site; a chemical cleavage site; or a mechanical cleavage site.

Item 29. The composition of Item 28, wherein the electromagnetic cleavage site is a photocleavage site.

Item 30. The composition of Item 29, wherein the photocleavage site is an ultraviolet (UV) cleavage site.

Item 31. The composition of any one of Items 23-30, wherein the first or second label is a fluorescent label.

Item 32. The composition of any one of Items 23-31, further comprising: a background reducing agent comprising a nucleotide sequence complementary to a nucleotide sequence of a portion of a first probe present between the cleavage site and the first label.

Item 33. The composition of any one of Items 23-32, further comprising: a background reducing agent comprising a nucleotide sequence complementary to a nucleotide sequence of a portion of a second probe present between the cleavage site and the second label.

Item 34. The composition of any one of Items 25-33, further comprising: a background reducing agent comprising a nucleotide sequence complementary to a nucleotide sequence of a portion of a subsequent probe present between the cleavage site and the subsequent label.

Item 35. A kit, comprising:
the probe-set composition of any one of Items 23-34;
a background-reducing agent;
a coverslip;
one or more target-specific binding partners;
one or more buffers;
one or more reagents for increasing the number of nucleic acid barcodes of a target-specific binding partner;
one or more cleavage agents;
a nuclear counterstain; and
instructions for use.

Item 36. The kit of Item 35, wherein the background-reducing agent is linked to a solid phase.

Item 37. The kit of Item 36, wherein the solid phase is selected from a coverslip; a particle and a slide.

Item 38. The kit of Item 35, wherein the background-reducing agent is in liquid phase.

Item 39. A background reducing agent, comprising a nucleotide sequence complementary to a released label of a first probe of the composition of any one of Items 23-31, and a quench material.

Item 40. A background reducing agent, comprising a nucleotide sequence complementary to a released label of a second probe of the composition of any one of Items 24-31, and a quench material.

Item 41. A background reducing agent, comprising a nucleotide sequence complementary to a released activated label of a probe of the composition of Item any one of Items 25-31, and a quench material.

Item 42. A method for detecting a plurality of target molecules, the method comprising:
(a) contacting a sample with two or more target-specific binding partners, wherein each target-specific binding partner comprises a nucleic acid barcode; and is specific for a different target molecule;

(b) contacting the sample with one or more probe-sets wherein each probe in a probe-set is specific for a different target-specific binding partner, and wherein each probe-set comprises:

a first probe, comprising:
  a nucleic acid sequence complementary to a nucleic acid barcode of a corresponding target-specific binding partner;
  a first label; and
  a cleavage site for a first cleavage agent, wherein the first cleavage agent is capable of suppressing the first label, and a second probe comprising:
  a nucleic acid sequence complementary to a nucleic acid barcode of a corresponding target-specific binding partner;
  a second label;
  a quench moiety, wherein the quench moiety renders the second label undetectable; and
  a cleavage site for the first cleavage agent, wherein the first cleavage agent is capable of releasing or suppressing the quench moiety, whereby the second label is rendered detectable;
  and optionally comprises a cleavage site wherein a second cleavage agent is capable of releasing or suppressing the second label;

(c) detecting signals corresponding to labels of the first probes of each of the one or more probe-sets;

(d) contacting the sample with a first cleavage agent, thereby suppressing the labels of the first probes in each of the one or more probe-sets; and releasing or suppressing the quench moieties of the second probes in each of the one or more probe-sets, thereby activating signals corresponding to the second labels; and (e) detecting signals corresponding to the labels of the second probes of each of the one or more probe-sets.

Item 43. The method of Item 42, wherein one or more of the probe-sets further comprises a third probe, comprising:

(f) in step (b), contacting the sample with a third probe contained in one or more probe-sets, wherein the third probe comprises:
  a nucleic acid sequence complementary to a nucleic acid barcode of a corresponding target-specific binding partner;
  a third label;
  a quench moiety, wherein the quench moiety renders the third label undetectable; and
  a cleavage site for a second cleavage agent, wherein the second cleavage agent is capable of releasing or suppressing the quench moiety, whereby the third label is rendered detectable;
  and optionally comprises a distinct cleavage site wherein a distinct cleavage agent is capable of releasing or suppressing the third label of one or more probe-sets; and (g) after step (e), contacting the sample with a second cleavage agent, thereby suppressing the labels of the second probes in each of the one or more probe-sets; and releasing or suppressing the quench moieties of the third probes in one or more probe-sets, thereby activating signals corresponding to the third labels; and (h) detecting signals corresponding to the third labels.

Item 44. The method of Item 43, wherein one or more of the probe-sets further comprise a subsequent probe, comprising:

(i) in step (b), contacting the sample with a subsequent probe contained in one or more probe-set, wherein the subsequent probe comprises:
  a nucleic acid sequence complementary to a nucleic acid barcode of a corresponding target-specific binding partner;
  a subsequent label; and
  a quench moiety, wherein the quench moiety renders the subsequent label undetectable; and
  a cleavage site, wherein a subsequent cleavage agent is capable of releasing or suppressing the quench moiety, whereby the subsequent label is rendered detectable;
  and optionally comprises a distinct cleavage site wherein a distinct cleavage agent is capable of suppressing activated labels from probes in the sample;

(j) contacting the sample with a subsequent cleavage agent, thereby suppressing activated labels of the probes in each probe-set; and releasing the quench moieties of the subsequent probes in each probe-set, thereby activating signals corresponding to the subsequent labels; and (k) detecting signals corresponding to the subsequent labels; and (l) optionally repeating steps (i) through (k).

What is claimed is:

1. A method for detecting a plurality of target molecules, the method comprising:
   (a) contacting a sample with two or more target-specific binding partners, wherein each target-specific binding partner comprises a nucleic acid barcode; and is specific for a different target molecule;
   (b) contacting the sample with one or more probe-sets wherein each probe in a probe-set is specific for a different target-specific binding partner, and wherein each probe-set comprises:
   a first probe, comprising:
       a nucleic acid sequence complementary to a nucleic acid barcode of a corresponding target-specific binding partner;
       a first label; and
       a cleavage site for a first cleavage agent, wherein the first cleavage agent is capable of releasing or suppressing the first label, and
   a second probe comprising:
       a nucleic acid sequence complementary to a nucleic acid barcode of a corresponding target-specific binding partner;
       a second label; a quench moiety, wherein the quench moiety renders the second label undetectable; and
       a cleavage site for the first cleavage agent, wherein the first cleavage agent is capable of releasing or suppressing the quench moiety, whereby the second label is rendered detectable; and optionally comprises a cleavage site for a second cleavage agent wherein the second cleavage agent is capable of releasing or suppressing the second label;
   (c) detecting signals corresponding to labels of the first probes of each of the one or more probe-sets;
   (d) contacting the sample with a first cleavage agent, thereby
   releasing or suppressing the labels of the first probes in each of the one or more probe-sets; and
   releasing or suppressing the quench moieties of the second probes in each of the one or more probe-sets, thereby activating signals corresponding to the second labels, and
   (e) detecting signals corresponding to the labels of the second probes of each of the one or more probe-sets.

2. The method of claim 1, wherein one or more of the probe-sets further comprises a third probe, and the method further comprises:
   (f) in step (b), contacting the sample with the third probe comprising:
       a nucleic acid sequence complementary to a nucleic acid barcode of a corresponding target-specific binding partner;
       a third label; and
       a quench moiety, wherein the quench moiety renders the third label undetectable; and
       a cleavage site for the second cleavage agent, wherein the second cleavage agent is capable of releasing the quench moiety, whereby the third label is rendered detectable;
       and optionally comprises a distinct cleavage site for a distinct cleavage agent capable of releasing the third label; and
   (g) after step (e), contacting the sample with a second cleavage agent, thereby releasing the labels of the second probes in each of the one or more probe-sets; and releasing the quench moieties of the third probes in one or more probe-sets, thereby activating signals corresponding to the third labels; and
   (h) detecting signals corresponding to the labels of the third probes of one or more probe sets.

3. The method of claim 2, wherein one or more of the probe-sets further comprise a subsequent probe, and the method further comprises:
   (i) in step (b), contacting the sample with a subsequent probe contained in one or more probe-set, wherein the subsequent probe comprises:
       a nucleic acid sequence complementary to a nucleic acid barcode of a corresponding target-specific binding partner;
       a subsequent label; and
       a quench moiety, wherein the quench moiety renders the subsequent label undetectable; and
       a cleavage site for a subsequent cleavage agent, wherein the subsequent cleavage agent is capable of releasing the quench moiety, whereby the subsequent label is rendered detectable;
       and optionally comprises a distinct cleavage site for a distinct cleavage agent capable of releasing activated labels from probes in the sample;
   (j) contacting the sample with a subsequent cleavage agent, thereby releasing activated labels of the probes in each probe-set; and releasing the quench moieties of the subsequent probes in each probe-set, thereby activating signals corresponding to the labels of the subsequent probes in each probe-set; and
   (k) detecting signals corresponding to the labels of the subsequent probes of each probe-set; and
   (l) optionally repeating steps (i) through (k).

4. The method of claim 2, wherein the two or more of the first, second, and third detectable labels of a probe-set are the same.

5. The method of claim 2, wherein the two or more of the first, second, and third detectable labels of a probe-set are different.

6. The method of claim 3, wherein two or more of the first, second, third, and subsequent labels are the same.

7. The method of claim 3, wherein two or more of the first, second, third, and subsequent labels are different.

8. The method of claim 1, wherein the first and second detectable labels of a probe-set are the same.

9. The method of claim 1, wherein the first and second detectable labels of a probe-set are different.

10. The method of claim 1, further comprising washing the sample after contacting the sample with the first cleavage agent and/or after contacting the sample with the second cleavage agent.

11. The method of claim 1, wherein the sample is not washed after contacting the sample with the first cleavage agent and/or after contacting the sample with the second cleavage agent.

12. The method of claim 11, wherein a coverslip is present on the sample and the coverslip is not removed.

13. The method of claim 1, further comprising increasing the number of nucleic acid barcodes on a target-specific binding partner, wherein multiple copies of a corresponding probe bind to multiple copies of the nucleic acid barcode.

14. The method of claim 13, wherein the number of nucleic acid bar codes is increased using rolling circle amplification, primer exchange reaction, hybridization chain reaction, or DNA branching.

15. The method of claim 1, wherein the released label of a first probe comprises a nucleotide sequence.

16. The method of claim 15, further comprising contacting the sample with a background-reducing agent comprising a nucleotide sequence complementary to that of the released label of the released first probe, wherein binding of the background-reducing agent to the released label of the released first probe quenches the signal of the label.

* * * * *